United States Patent [19]

Hill

[11] Patent Number: 5,714,691
[45] Date of Patent: Feb. 3, 1998

[54] METHOD AND SYSTEM FOR ANALYZING A TWO PHASE FLOW

[75] Inventor: Wayne S. Hill, Westborough, Mass.

[73] Assignee: Foster-Miller, Inc., Waltham, Mass.

[21] Appl. No.: 736,523

[22] Filed: Oct. 24, 1996

Related U.S. Application Data

[62] Division of Ser. No. 333,213, Nov. 2, 1994, Pat. No. 5,600,073.

[51] Int. Cl.⁶ ............................................. G01F 1/74
[52] U.S. Cl. ............................................. 73/861.04
[58] Field of Search ................. 73/861.04, 29.01, 73/659, 30.03, 23.2, 24.01, 24.04

[56] References Cited

U.S. PATENT DOCUMENTS

| | | | |
|---|---|---|---|
| H608 | 3/1989 | Goolsby | 367/89 |
| 3,392,572 | 7/1968 | Brown | 73/29.01 |
| 4,576,036 | 3/1986 | Huang et al. | 73/29.01 |
| 4,688,418 | 8/1987 | Cheung et al. | 73/29.01 |
| 4,753,106 | 6/1988 | Brenner et al. | 73/29.01 |
| 5,390,547 | 2/1995 | Liu | 73/861.04 |
| 5,419,197 | 5/1995 | Ogi et al. | 73/659 |
| 5,600,073 | 2/1997 | Hill | 73/861.04 |

*Primary Examiner*—Ronald L. Biegel
*Assistant Examiner*—Jewel V. Artis
*Attorney, Agent, or Firm*—Iandiorio & Teska

[57] ABSTRACT

A method of and system for analyzing a two-phase flow in a conduit in which acoustic energy is transmitted through a conduit and into the flow therein; return echoes are detected, one or more flow indicator quantities are computed from the return echoes; and the mass flow rate and/or the flow quality is determined from the computed flow indicator quantities.

27 Claims, 15 Drawing Sheets

METHOD AND SYSTEM FOR ANALYZING A TWO PHASE FLOW

This is a division of application Ser. No. 08/333,213, filed Nov. 2, 1994, now U.S. Pat. No. 5,600,073.

GOVERNMENT RIGHTS

This material is based upon work supported by the United States Air Force under Contracts Number F29601-91-C-0055 and Number F29601-92-C-0035. The Government, therefore, has certain rights in this invention.

FIELD OF INVENTION

This invention relates to a method and system for analyzing a two phase flow and for determining the quality and mass flow of a two phase flow using ultrasonic techniques, and other sensors.

BACKGROUND OF INVENTION

A two phase flow in a conduit is a flow which includes both gas and liquid, or gas and solid, or liquid and solid. An example of a gas/liquid two phase flow is water and air flowing in a pipe; an example of a gas/solid two phase flow is coal particles and air flowing in a pipe. Ultrasonic methods for determining the presence of a two phase flow in a conduit are known. See, e.g., US statutory invention registration No. H608. Essentially, an ultrasonic pulse is sent transversely through a pipe and if the flow is single phase (i.e. all liquid), a return pulse is detected after a time lag as a return echo which is strong and reasonably sharp off the far wall of the pipe. If gas bubbles are entrained in the liquid, there are multiple small reflections and diffusion or attenuation of the main return echo off the far wall of the pipe. If a two phase flow with a defined gas/liquid interface is present in the pipe, the return echo is fairly strong but earlier in time than in the situation where there is only liquid flow since the return echo bounces off the gas/liquid interface instead of the far wall of the pipe. Finally, if the flow has a defined gas/liquid interface and also gas bubbles in the liquid, there are multiple small reflections due to the bubbles in the liquid and the return echo is both attenuated and earlier in time than would be the case with only liquid flow. Such measurement methods, however, which only detect the presence of a two-phase flow, do not completely define the two phase flow.

Quality is the mass fraction of the two-phase flow that is in the gaseous phase. Quality together with mass-flow determines the amount of energy (enthalply) that is convected by the flow and thus is a key variable used to define the status of the flow system. Accordingly, quality and/or mass flow measurements are needed to fully define the flow. One reason that mass flow rate and the quality measurements are needed is to adjust the rate of one phase of the flow in a system.

A typical liquid/gas two phase flow comprises a liquid film in contact with part or all of the conduit wall (depending on flow parameters and flow orientation with respect to gravity). The liquid is largely separate from a continuous or intermittent vapor flow. Since an identifiable liquid-vapor interface exists, it is possible to analyze the geometry, flow rate, and axial pressure drop behavior of the liquid and vapor flow separately, equating boundary conditions as appropriate. If the thickness of the liquid flow in the conduit can be determined, various flow models can be used to predict film thickness versus quality for a number of mass flow rates. See, for example, Wallis, G. B., *One-dimensional Two-Phase Flow*, McGraw-Hill, New York, N.Y., 1969, pages 51–54, and 315–374; Lockhart, R. W. and Martinelli, R. W, "Proposed Correlation of Data for Isothermal Two Phase, Two Components Flow in Pipes", Chemical Engineering Progress, Volume 45, No. 1, 1949, pages 39–48; and Deissler, R. G., "Heat Transfer and Fluid Friction for Fully Developed Turbulent Flow of Air and Super Critical Water with Variable Fluid Properties", Transactions, ASME volume 76, No. 1, 1954, page 73.

But the precursor step of detecting the thickness of the liquid flow using ultrasonic methods is troublesome. The presence of bubbles of gas in the liquid flow, the presence of large waves of liquid traveling in the conduit, small scale thickness changes in the liquid/vapor interface, and other similar "chaotic" conditions within the conduit severely affect the ability to determine film thickness using ultrasonic techniques. If one or more of these conditions are present within the conduit, a plot of the return echoes from an ultrasonic transducer is not a good indicator of film thickness. Moreover, a low flow rate with a high quality results in a highly chaotic flow as does a high flow rate with a low quality. Such chaotic flows render known film thickness measurement techniques unreliable.

Therefore, a trace of the return echoes from such a chaotic flow alone is seemingly not a good indicator of film thickness. Other techniques for measuring the thickness of the liquid film that is usually in contact with the wall of the conduit include sampling, thermal probes, film conductivity or capacitance measurements, and gamma densitometry. Although each of these techniques exhibits strengths and weaknesses, no technique offers the advantages of reflective-mode ultrasound. Ultrasound techniques are non-invasive, offer rapid response, excellent long term accuracy and sensitivity, and are applicable to all working fluids over a very broad range of temperatures. Moreover, even if non-ultrasonic thickness measurement techniques are used, the various flow models used to evaluate flow quality and mass flow rates are based on a number of assumptions which can lead to inaccuracies. On the other hand, quality and/or mass flow measurements cannot be accurately taken without measuring film thickness or a related parameter, void fraction. Flow meters, for example, do not indicate how much of the flow is liquid or gas and flow meters cannot be used in all situations.

A typical gas/solid two phase flow, such as coal particles entrained in an air flow, generally comprises a rope like structure of coal particles travelling in the pipe. There are no current techniques which accurately measure the amount of coal in the pipe. Trial and error methods commonly used in coal power plant operation, can result in poor efficiency and air pollution. In order to optimize combustion, the amount of coal and the amount of air delivered to the burner must be known.

Therefore, in addition to determining the presence of a two phase flow, considerable research has been performed on various means of actually measuring two-phase flows. These efforts have largely attempted to characterize an average value of some aspect of the flow, such as a pressure drop, void fraction, film thickness, velocity, or density. One problem with this approach is that knowledge of any single value is not sufficient to define a two-phase flow. Two-phase flows comprise two separate flows (of phase A and Phase B) that interact in extremely complex ways. If average values are used, at least two independent quantifies must be measured to define the flow. In addition, a given pair of observations, such as a pressure drop and a velocity, often does not provide a sensitive indication of the flow rates of phase A and phase B for a broad range of conditions. Thus, different combinations of observations are often needed for different flow conditions.

There are applications that can be well served by suitably developed instruments based on currently known avenging techniques. However, there are many more applications for which combinations of currently available averaging measurements will not provide desirable results. For example, some applications demand a completely non-invasive flow measurement. Others may be geometrically constrained, so that only instruments of a given size or shape may be used. Other applications may require accurate flow measurement over an extremely broad range of flow conditions. Still others may be very cost-driven, so that the instrument must be very inexpensive. The current invention offers the advantage that any meaningful measurement technique, used rapidly and persistently, can be used to determine the flows of both phases. Since every application permits at least some meaningful flow observation to be made, the current invention ensures that a practical instrument can be developed.

The approach of the subject invention arises from simple, but profound observations about two-phase flows. First, they are deterministic, in that they satisfy the laws of physics. Thus, while their evolution is extremely complex, there is an underlying order to the flow behaviors. The behavior of a given wave, particle, or bubble, although complicated, is not truly random.

Second, since they are deterministic and behave in a complex fashion, they are likely to be chaotic. The word "likely" is used here because it has not yet been proven in generality that fluid turbulence satisfies the mathematical definition of chaos. It is not yet known what (if any) kinds of complex behaviors are possible that are neither chaotic nor random. It currently is not possible to make generalities about he behaviors of such a system. For want of a more conclusive answer from topologists, and since the view of two-phase flows as chaotic is consistent with the evidence so far available, the current invention assumed that the two-phase flows of interest are chaotic.

Two-phase flows are dissipative, i.e. given the opportunity, any work that is imposed on them is eventually lost to viscosity. Thus, given an arbitrary initial condition (e.g., means of mixing at the inlet to the flow conduit), a two-phase flow will settle into a pattern of behavior that is similar to that of other flows with the same flows of phase A and phase B but different initial conditions. Actually, it is difficult to prove this conclusively without generating many flow conditions with a variety of initial conditions and comparing their properties in detail. However, it is a basic tenet of the arts of fluid mechanics and two-phase flow that this is the case: if this were not the case, it would not be possible to generate models or correlations of two-phase flow behaviors. This is also consistent with the properties of dissipative chaotic systems.

If two-phase flows are dissipative and chaotic, then key statements can be made about their behaviors. Principal among these is the existence of a single underlying behavior, a "strange attractor", the shape of which changes as flow parameters change. The strange attractor is an extremely complicated path (in mathematical phase space) that defines all trajectories of the system with time. It is limited to a finite portion of phase space and is a single unending, open (i.e., never repeating) path in which points that are initially near one another diverge rapidly from one another with time (called sensitivity to initial conditions). The conclusions that can be drawn from the existence of a strange attractor are far-reaching. The principal conclusion for current purposes is that any observation of the system behavior, made over a period of time, is a mapping of the strange attractor. If the observation is made with constant time increment between measurements, it is a smooth mapping. Any smooth mapping of a strange attractor contains an amount of information about the system behavior that is comparable to any other smooth mapping with the same time increment and measurement sensitivity. Thus, any of a variety of measurement methods may be used with a two-phase flow with equal conviction that meaningful information is obtained.

This line of discussion is fairly well established in the art of chaos theory, but by itself is not sufficient to permit the measurement of two-phase flows. The reason for this is that the argument does not disclose how the evolution of the flow observations can be related to the flow conditions. In fact, various researchers have attempted to relate two-phase flow conditions to time-series measurement. The best known of these are Jones, O. C. and Zuber, N., "The Interrelation between void fraction fluctuations and flow patterns in two-phase flow" Int'l J. of Multiphase Flow, v2, page 273–306, 1975; Hubbard, MG., and Dulder, A. E., "The Characterization of Flow regimes for Horizontal two-phase flow: 1. statistical analysis of wall pressure fluctuations", Proceedings of the 1966 Heat Transfer and Fluid Mechanics Institute, Saad, M. A. and Miller, J. A. eds., Standard University Press, pages 100–121, 1966. Jones and Zuber identified liquid-gas flow regimes from the probability density function of X-ray attenuation measurements. Hubbard and Dukler identified flow regimes from frequency spectra of pressure signals from liquid-gas two-phase flows. In neither of these cases was the flow rate of either or both phases determined.

The technical literature has many references describing efforts to examine or develop instruments of various kinds to measure or characterize two-phase flows. Overviews include Hsu, Y. Y., and Graham, R. W., Chapter 12: Instrumentation for Two-Phase Flow, in *Transport Processes in Boiling and Two-Phase Systems*, McGraw-Hill, 1976; and Mayinger, F., Chapter 16: Advanced Optical Instrumentation, in *Two-Phase Flow and Heat Transfer in the Power and Process Industries*, Bergles, A. E., et al, editors, Hemisphere Publishing Company, 1981. The bulk of these efforts have generated results of sufficiently limited application to have remained largely of research interest. True two-phase flowmeters, i.e., instruments that purport to define the flows of both phases A and B, are not widely available on the commercial market.

In industrial practice, the most widely used instruments for two-phase flows have been photon attenuation instruments. These instruments determine the attenuation of photons (typically microwaves or gamma rays) as they pass through the flow. The greater attenuation of one phase than the other (essentially from higher density) is used to characterize the portion of the flow channel cross section that is filled with each phase. Alternatively, this may be viewed as characterizing the average density of the flow. Depending upon the specific geometry of the instrument, it may be rendered more or less sensitive or the distribution of the phases across the flow channel, and thus may be used to identify the flow regime (e.g., bubbly, slug, stratified, annular, or mist flows). These instruments provide only a rough indication of the flow condition, because their sensitivity to the amount of each phase that is present is limited. In particular, gamma densitometers are highly sensitive to even trace quantities of lead in a flow, severely limiting their accuracy in many applications of interest (most notably in petroleum pipelines). Despite the limitations of these instruments in their originally intended embodiment, they could be used to advantage with the current invention to accurately determine the flows of phases A and B.

To generate useful information about the flow rates of phases A and B, an attenuation measurement must be combined with some indication of flow velocity. Such an indication may be obtained by making attenuation measurements at two closely spaced stations along the flow duct and cross-correlating the resulting signals. The time delay of the peak in the cross-correlation curve corresponds to an approximate time delay for flow propagation. Dividing the spacing of the instruments by this time delay provides a characteristic velocity. The average flow density and this velocity can be correlated to the flow rates of phases A and B. Correlation is needed to correct for the inevitable "slip" that occurs between phases (because they do not flow with identical velocity).

Even with suitable calibration, the accuracy of cross-correlated attenuation measurements is limited because of the poor sensitivity of the density measurement for many flow conditions. This limited accuracy is implied in U.S. Pat. No. 4,683,759 to Skarvaag et at, wherein, this basic idea is used to measure liquid-gas two-phase flows. However, the determination of liquid and gas flow rates is discussed for only one specific flow regime, called slug flow, in which the liquid and gas flows are largely intermittent, and the peak in the cross-correlation function quite sharp.

Other instrument systems have been devised to observe two-phase flows. In U.S. Invention registration H608 to Goolsby, an ultrasonic measurement technique is used to determine whether gas is present in a liquid flow. In this instrument, echo-mode ultrasound is used to determine the location of the second major reflection interface (the first being between the liquid and the tube wall). If the time-of-flight of the acoustic wave is less than that associated with a full tube (second reflection from the far wall), then a liquid-gas interface is present. Actually, this approach has been used to study two-phase flows quantitatively for quite a few years.

In U.S. Pat. No. 4,193,291 to Lynnworth, an ultrasonic method of determining flow density is described. This technique is based on the different attenuation rates of torsion waves in a body depending upon the density of the fluid in which the body is immersed. Various embodiments are described that render the instrument more or less sensitive to the distribution of the phases in the flow duct. This instrument is limited to liquid-liquid or liquid-gas two-phase flows. One unfortunate aspect of this instrument is its intrusiveness into the flow. The protrusion of the instrument into the flow raises the potential for damage to the instrument from debris carried by the flow, generates an undesirable pressure drop and flow disruption, and requires seals between the instrument and the flow duct which reduce the reliability of the flow system. Another unfortunate aspect of this instrument is that no single embodiment is described that determines the average density across the entire flow cross section. Thus, each embodiment is applicable to a limited range of flow regimes. Further, the issue of fluid wetting is not addressed: if the liquid wets the material of the sensor, the apparent density may be skewed strongly toward the liquid density. Even with these limitations, the mechanism of this measurement approach could be used with the current invention to provide an accurate determination of the flow rates of phases A and B.

The aforementioned patent states that the density measurement may be combined with acoustic velocimetry to determine the flow rates of both phases. In acoustic velocimetry, an acoustic wave is propagated by one transducer downstream through the flow and its time-of-flight to another transducer measured. A second wave is propagated upstream to determine the propagation time against the flow. Comparison of these propagation times determines both the effective speed of sound of the flow and its propagation velocity. If acoustic velocimetry works in two-phase flows at all, the measurements would be very sensitive to the flow regime. For example, in annular flow, a continuous liquid film is in contact with the flow duct wall. Any acoustic waves that enter the flow will effectively "short circuit" through the liquid (with its very high sonic velocity and relatively low attenuation) so that only the liquid velocity (skewed by the acoustic wave path) would be measured. By contrast, in stratified flow, a liquid flow on the bottom of the flow duct is effectively separated from a gas flow in the top of the duct. If acoustic waves traveling through the liquid can couple sufficiently with the gas flow, then a velocity that is an average of the liquid and gas velocities will be measured. This velocity would be quite different from (much higher than) that of an annular flow, even though annular flows often occur at much higher velocities. Thus, the calibration of the instrument output with different flow conditions would involve some very strong nonlinearities likely to result in poor accuracy.

U.S. Pat. No. 4,991,124 to Kline describes a different ultrasonic instrument for determining a fluid density. This technique is based on determining the velocity of sound and rate of attenuation of acoustic energy in the fluid. Because this technique relies on multiple reflections of the acoustic energy, which would be extremely difficult to detect in two-phase flows, it probably could not be applied to a two-phase flow.

AEA Technology, of the United Kingdom, has publicized a two-phase flowmeter for use in oil and gas fields [Anonymous, "Non-Intrusive Meter Measures Oil and Gas Flows", competitive Edge, Issue 4, pg. 3, Spring, 1994. This instrument uses a pulsed neutron beam which counts hydrogen, carbon, oxygen, and chlorine atoms passing the sensing point. Short bursts of radiation are used to activate oxygen atoms, which can be tracked as they move to define a flow velocity (a second measurement method). This instrument employs two averaging techniques to determine the flow rates of (potentially) several phases. However, it depends upon the phases being of distinct compositions to define their flow rates separately. If the two phases were of the same composition (a so-called single-component two-phase flow), then only a total flow measurement would be obtained. While this system may prove effective for its intended application in oil fields, its cost, complexity, and operational limitations will limit its use elsewhere.

SUMMARY OF INVENTION I

It is therefore an object of this invention to provide a method and a system for analyzing a two phase flow to determine the quality and mass flow of the flow.

It is a further object of this invention to provide such a method and system for determining the quality and mass flow of a two phase flow using non-invasive sensors.

It is a further object of this invention to provide such a method and system for determining the quality and mass flow of a two phase flow which results in reliable measurements even in the presence of a chaotic two phase flow in a conduit.

It is a further object of this invention to provide such a method and system for determining the quality and mass flow of a two phase flow without the need for using various flow models and analysis techniques which are based on a number of assumptions.

This invention results from the realization that on first blush, the ultrasonic thickness trace for the return echoes in a chaotic two phase flow does not appear to accurately show the thickness of the fluid flow, but that on further investigation, certain indicators about the nature of the flow are actually present in the thickness traces over time and these indicators, such as the avenge number of good thickness readings in a row, the avenge change in sequential good readings, and the average fraction of the readings that are good, can be used together to accurately measure mass flow and flow quality. This invention also results from the fundamental realization that mass flow and flow quality can be directly determined from the thickness trace without the need for complicated analysis techniques which rely on a number of assumptions and without the need for invasive measurement techniques. This invention also results from the realization that means other than ultrasonic thickness traces may now be used to obtain flow indicators which can be used to characterize and describe the flow.

Finally, this invention results from the realization that the flow indicator quantities can be detected by a number of different types of sensors; that the flow indicator quantifies can be detected for a conduit containing any type of a two phase flow and even immiscible flows; and that the analysis of the flow indicator quantities can be used to evaluate the flow. Once the flow is analyzed, a feed-back system can be employed to regulate the flow.

The subject invention relates to the measurement of two-phase flows which may be mixtures of a liquid with a gas or vapor, a liquid with solid particles, two immiscible liquids, or a gas with solid particles. This invention is equally applicable to flows in which the two phases (e.g., A and B) are of the same or different composition. It relates to situations in which such flows are constrained within a flow channel or duct, although it is likely that the concept may be extended for application to either free stream flows or flows around a submerged or immersed body. It is also likely that the concept may be extended to flows of three or more constituents, or to single-phase (liquid or gas-only) flows.

The fundamental concept of the subject invention is that given a suitable flow observation made persistently, the measurement values and their variation with time reflect the phenomena occurring in the flow and, therefore, the flow condition. The flow condition usually is defined by the flow rates of the two phases. The temperature and/or pressure may also be needed to define the properties of the two phases. This measurement approach depends on an unsteady, complex flow structure for its operation. Such a flow structure is usually associated with fluid turbulence. However, even many two-phase flows that are considered laminar are characterized by gentle variations, and so should be amendable to the subject invention. In addition, localized turbulence can be induced in many otherwise laminar flows through such devices as bluff bodies, static mixers, orifices, elbows, or other flow disruptions. Thus, the measurement method described herein should have a very broad range of application.

It is a principal object of the current invention to disclose a measurement approach that permits the reliable determination of the relationship between time-series observations and the flows of both phases of a two-phase flow. The bulk of the work discussed below has been performed with liquid-gas two-phase flows using an ultrasonic thickness measurement as the method of flow observation. As the preceding disclosure describes, the current invention is not limited to such flows or a single method of flow observation. The subject invention is applicable to all two-phase flows with intrinsic time-varying behaviors, and all observation methods that meaningfully reflect the structure of the flow. Consequently, alternative observation methods for various situations and applications are detailed below, as well as the anticipated response of such instruments and means of relating the observations to the flow conditions.

This invention features a method of analyzing a two-phase flow in a conduit and may suitably comprise, consist essentially of, or consist of transmitting acoustic energy through the conduit and into the flow therein; detecting return echoes; computing from the return echoes, one or more flow indicator quantities derived from return echoes; and determining, from the computed flow indicator quantities, at least one of the mass flow rate and the flow quality. The flow indicator quantities are selected from one or more of the average number of good thickness readings, the average change in sequential good readings, and the average fraction of the total readings that are good readings, wherein a good reading is defined as a detected return echo which is assumed to be indicative of the thickness of liquid flow in the conduit.

The method further includes calculating the quantity of the average absolute value change in sequential good readings divided by the average number of good readings for discriminating between mass flow and quality. The flow indicator quantities may further include the RMS of good thickness readings, the RMS change in sequential good readings, the average number of good readings in a row, the average number of bad readings in a row, and the characteristic autocorrelation time. The step of determining includes matching a number of the flow indicator quantities with known flow conditions for estimating the mass flow and quality of the two phase flow in the conduit; the step of matching includes using a neural network trained to match a number of said flow indicator quantities with known flow conditions to estimate mass flow and quality, and the step of computing includes obtaining data in the form of the average number of good thickness readings in a row compared to flow quality and the average change in sequential good readings compared to flow quality.

This invention also features a system for analyzing a two phase flow in conduit comprising means for transmitting acoustic energy through the conduit and into the flow therein; means for detecting return echoes; means for computing, from the return echoes, one or more flow indicator quantities; means, responsive to the means for computing, for determining one of the flow quality and the mass flow rate based on the flow indicator quantities. The means for transmitting acoustic energy includes a plurality of transducers circumferentially and/or axially coupled to the conduit and further includes means for firing the transducers sequentially. The means for detecting return echoes evaluates return echoes indicative of the thickness of the liquid flow in the conduit.

The means for computing calculates one or more of the following flow indicator quantities: the average number of good thickness readings, the average change in sequential good readings, and the average fraction of the total readings that are good readings, wherein a good reading is defined as a detected return echo.

The means for computing calculates the quantity of the average absolute value change in sequential good readings divided by the average number of good readings for discriminating between mass flow and quality and the means for determining includes a neural network which takes as input one or more of the calculated flow indicator quantities and applies a pattern matching algorithm to predict one of the flow quality and the mass flow based on actual flow qualities and mass flow rates patterns learned by the neural network.

This invention also features a method of determining the quality of a two-phase flow in a conduit comprising transmitting acoustic energy through the conduit wall and into the flow therein to generate from the flow return echoes, detecting the return echoes from the flow, computing the two-phase flow mass flow rate, and determining from the return echoes at least one of the mass flow rate and the flow quality.

Transmitting acoustic energy includes providing ultrasonic pulses to the outer conduit wall and detecting return echoes includes determining the fraction of echoes above a predetermined echo strength. Determining the mass flow rate includes resolving the two-phase flow rate from the fraction of return echoes above the predetermined echo strength. Determining the flow quality includes calculating the liquid film thickness on the conduit from the return echoes. Determining the flow quality further includes calculating the average change in calculated liquid film thickness and determining the flow quality further includes determining the average calculated film thickness and further includes determining the ratio of the average change to the average film thickness.

The flow quality determination method includes calculating one or more flow indicator quantities from the detected return echoes from the flow. The flow indicator quantities include one or more of: the average number of good thickness readings, the average change in sequential good readings, and the average fraction of the total readings that are good readings, wherein a good reading is defined as a detected return echo.

The method further includes calculating the quantity of the average absolute value change in sequential good readings divided by the average number of good readings for discriminating between mass flow and quality and the flow indicator quantities further include the RMS of good thickness readings, the RMS change in sequential good readings, the average number of good readings in a row, the average number of bad readings in a row, and the characteristic autocorrelation time. Determining the mass flow rate and the flow quality further includes applying one or more of the flow indicator quantities to a neural network for matching the flow indicator quantities with known flow conditions.

The system for determining the quality of a two-phase flow in a conduit according to this invention includes means for transmitting acoustic energy through the conduit wall and into the flow therein to generate from the flow return echoes; means for detecting the return echoes from the flow; and means for computing the two-phase flow mass flow rate; and means for determining from the return echoes at least one of the mass flow rate and the flow quality.

In a more comprehensive sense, this invention features a method for determining the mass flow rate and quality of a two-phase flow in a conduit comprising transmitting acoustic energy through the conduit wall and into the flow therein to generate from the flow return echoes, detecting the quantity of return echoes above a predetermined echo strength, determining from the quantity of return echoes the two-phase flow mass flow rate, calculating from the return echoes the liquid film thickness on the conduit wall and determining the average change in calculated liquid film thickness, the average calculated film thickness, and the flow quality from the ratio of the average change to the average film thickness.

DISCLOSURE OF PREFERRED EMBODIMENT

Other objects, features and advantages will occur to those skilled in the art from the following description of a preferred embodiment and the accompanying drawings, in which.

This invention broadly features a two-phase flow meter. Flow indicator quantities such as the presence of "waves" of liquid travelling in a liquid/gas two phase flow or "waves" of particles travelling in a solid/gas two-phase flow, and the period in between the passage of waves are detected by a number of different types of sensors including ultrasonic transducers, microphones, accelerometers, and the like. The flow indicator quantities, once detected, can be used to determine either the mass flow rate or the quality of the flow, or both. Or, in some implementations, the flow indicator quantifies can be used to detect a change in flow conditions. In the first embodiment, the two-phase flow meter is employed using ultrasonic detectors to determine mass flow rate and flow quality for a liquid/gas two phase flow in a conduit.

In this invention, determining the film thickness of a two phase flow in a conduit is only a first order evaluator of flow quality and/or mass flow. In a typical two phase flow, the presence of a steep fluid/vapor interface, the presence of a periodic waves of fluid traveling in the conduit, and the presence of vapor bubbles entrained in the liquid render film thickness measurements using ultrasonic methods difficult to interpret. But using ultrasonic techniques the film thickness traces themselves, although they may not accurately measure film thickness, were discovered to include a number of flow indicators which, if used together, allowed flow quality and/or mass flow to be determined through calibration.

Ultrasonic Two Phase Flow Meter

Figure 1:
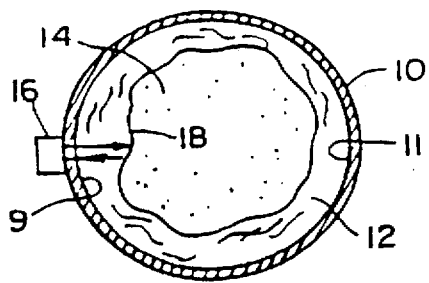
FIG. 1 is a cross-sectional schematic diagram of a typical two phase flow in a conduit.

FIG. 1 details a cross-sectional view of a two phase flow in conduit 10 with liquid 12 flowing on the interior periphery of the conduit wall and gas or vapor core 14 flowing proximate the center of the conduit.

Ultrasonic transducer 16 is first calibrated with conduit 10 empty to establish the pulse time delay in detecting a return echo from near wall 9 of an echo from the far wall 11 and then calibrated with conduit 10 completely filled with liquid to establish the time delay due to the sonic velocity of the liquid.

Figures 2, 3, 4:
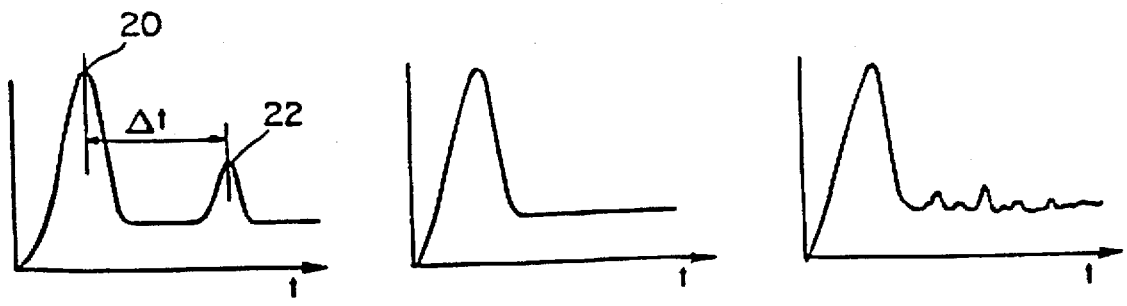
FIG. 2 is a graphical illustration of the transmitted and received pulse wave forms for a "good" film thickness reading.
FIG. 3 is a graphical illustration of a transmitted wave showing a lack of a return wave due to a return echo reflected away from the receiver.
FIG. 4 is a graphical illustration of multiple weak return echoes due to the presence of gas bubbles in the liquid flow.

A two phase flow is then introduced into the conduit 10 and the pulse time Δt, FIG. 2, between the initial pulse 20 and return echo 22 from the interface 18, FIG. 1 of the liquid 12 and gas 14 flow is measured.

The thickness of the liquid film h is then:

$$h = \frac{C\Delta t}{2} \qquad (1)$$

Where C is the velocity of sound in the liquid and Δt is the time between sending the ultrasonic pulse and receiving the echo. FIG. 2 depicts a "good" thickness reading, i.e. a reading in which there is a detected return echo that is fairly indicative of the thickness of liquid flow in the conduit. The return pulse 22 is fairly strong and sharp as shown.

If the interface between the liquid and gas flow as shown at 18 in FIG. 1 defines an inclined surface, however, the return echo may be reflected away from the receiver and never detected. In that case, the trace of the "return echoes" looks more like that shown in FIG. 3. On the other hand, if the interface between the liquid and gas flow as shown in FIG. 1 is rough or non-distinct, the return echo trace may appear as shown in FIG. 4. The presence of bubbles within the liquid film, waves, and other chaotic behaviors of the flow result in a number of "bad" readings which are not indicative of an accurate film thickness measurement.

In this invention, however, this information is still used and analyzed to fully characterize the flow and to accurately measure mass flow and flow quality.

This invention may be accomplished in a method of determining the quality and/or mass flow of a two-phase flow in a conduit using ultrasonic film measurement techniques. The mass flow rate and quality are separately determined from the combination of several quantities calculable from the raw data.

Figure 5:
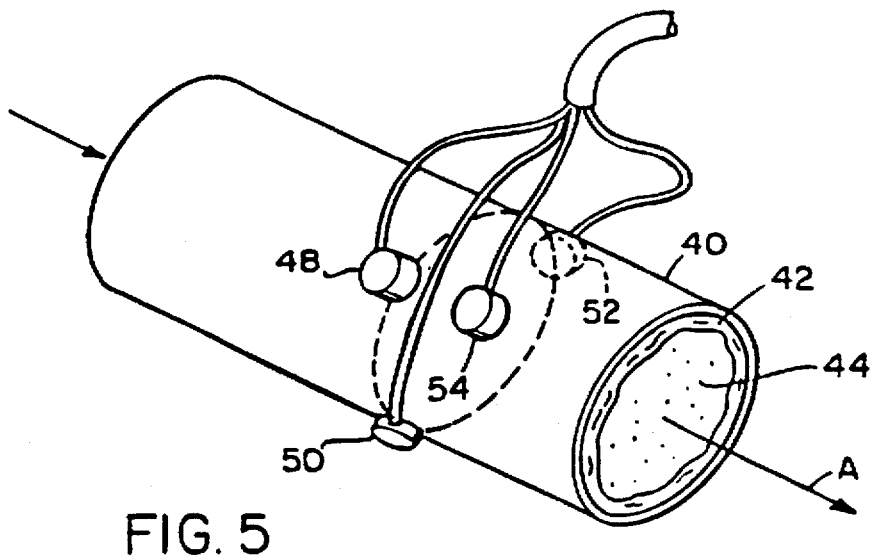
FIG. 5 is a schematic diagram of an ultrasonic film thickness measurement system according to this invention including possible enhancing options.

There is shown in FIG. 5 one embodiment of the ultrasonic film thickness measurement concept useful for the method and system of this invention. A two-phase flow is flowing in the direction of arrow A within circular cross section conduit 40. The flow comprises a liquid film 42 on the inner walls of conduit 40, and vapor flow 44. The flows are typically turbulent flows in which vapor bubbles are entrained within the liquid, and the surface of liquid 42 is often not smooth. Liquid droplets may be entrained in the vapor core.

Standard ultrasonic thickness measurement transducers are employed to make film thickness measurements that are then used to determine the mass flow rate and the quality of the flow within conduit 40. Preferably, multiple ultrasonic transducers are coupled to the outer wall of conduit 40 at different circumferential locations at one axial position. In this example, three such transducers 48, 50 and 52 are shown spaced circumferentially at one axial position around conduit 40. Fourth transducer 54 is placed directly downstream of transducer 48 to determine the characteristic film velocity. Transducers 48, 50 and 52 are fired sequentially. Axially displaced transducer 54 is fired at a later time than transducer 48. The outputs of transducers 48 and 54 are cross correlated, preferably using the domain analysis techniques as known in the art, to determine the flow velocity.

Figure 6:
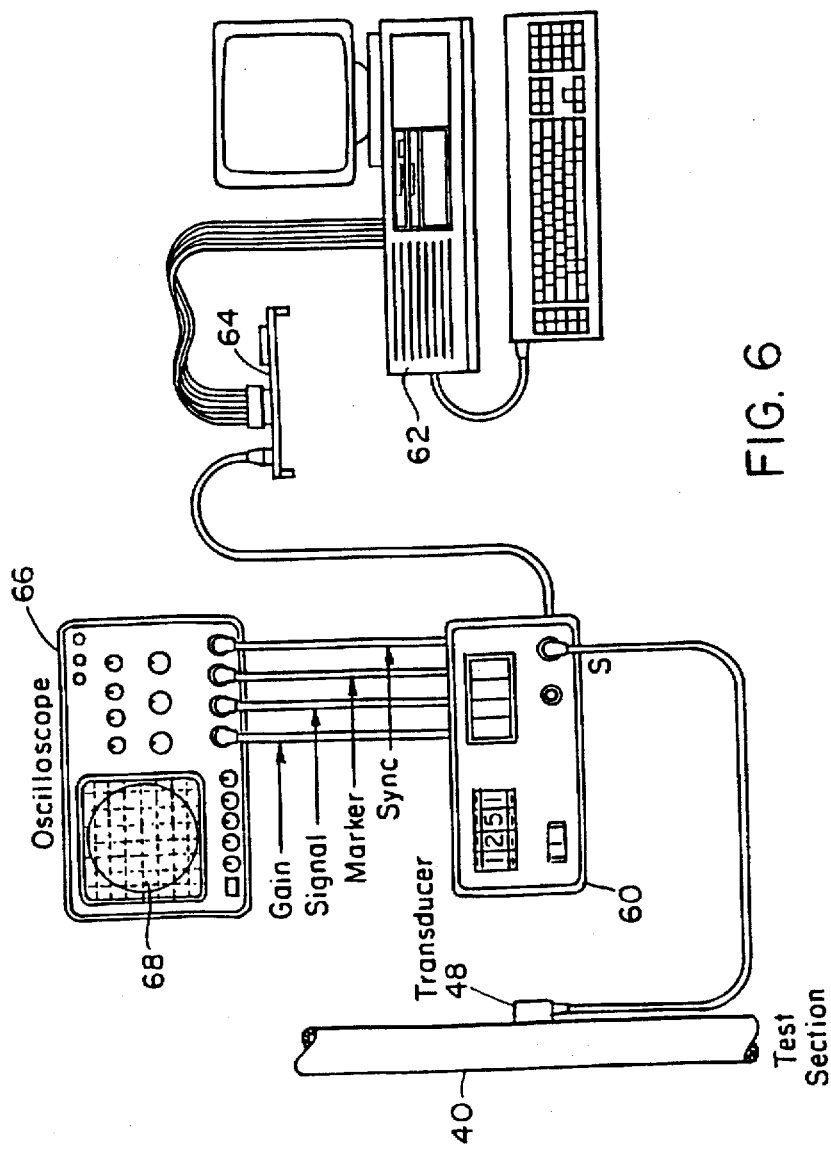
FIG. 6 is a diagram of the hardware used with the measurement system of FIG. 5 according to this invention.

The hardware for accomplishing film thickness measurements using the transducer arrangement of FIG. 5 is shown in FIG. 6. Typically, conduit 40 may be a horizontal, inclined, or vertical test section. For the measurements detailed in FIGS. 7 through 21, a clear polycarbonate tube of 0.875" inside diameter and 1.0" outside diameter and 26" long was used, thereby providing approximately 30 tube diameters for flow development upstream of the ultrasonic measurement point. The ultrasonic transducers such as transducer 48 were excited with an electrical pulse of a voltage on the order of 100 volts and very little energy, in the mid range of the instrument capability. The time delay provided by the solid wall between the transducer and the liquid film was accounted for by recording the pulse return time with the tube empty. The instrument was similarly calibrated for the sonic velocity of the liquid C, equation (1), by measuring the time delay with the tube filled with the liquid.

The apparatus of FIG. 6 was employed by introducing water and air at known pressures, temperatures and flows into the tube upstream of the test section. The water flow was measured using a turbine flow meter. The air flow was measured using an elbow flow meter. The air pressure and temperature in the elbow flow meter were measured to determine density and thus mass flow. The pressure and temperature of the air-water mixture in test section 40 were also measured so that, with known air and water flow rates, the flow conditions were completely defined. Ultrasonic pulser-receiver 60 is a Model 5222 ultrasonic gauge purchased from Panametrics Corp. in Waltham, Mass. This instrument is an analog instrument intended for operation with transducers with frequencies of between 1 and 20 MHz. The instrument was modified to run at a pulse repetition rate of 800 Hz. Transducer 48 was a 10 MHz transducer.

The signal from the pulser-receiver 60 was fed to a multiplexer 64 that allowed an adjustment of the gain of the analog signal to maximize the sensitivity of the digital record. Multiplexer 64 is a model EXP-16 card purchased from Keithley-Metrabyte Inc. of Taunton, Mass. A model DAS-8 analog to digital conversion card also purchased from Keithley-Metrabyte Inc. was installed in computer 62. This card generated a 12 bit digital output from an analog input voltage of from −5 to +5 volts. Unkelscope data acquisition software, available from Unkelscope Software Inc., Lexington, Mass. is used to control computer 62. This software was set up to record data at 1000 Hz and to generate records of 4096 readings each.

Three trace oscilloscope 66 was used to monitor the performance of pulser-receiver 60. Analog outputs from pulser-receiver 60 included a time-dependent gain, marker monitor, and receiver monitor. This oscilloscope was synchronized to the signals using a synchronizing output from pulser-receiver 60. The receiver monitor represents the actual ultrasonic waveform observed by the receiver section of the pulser-receiver. The marker is the point within the received signal where the receiver believes the echo is located. The location of the marker on the screen 68 corresponds to the thickness measurement. If the marker goes off the screen, the echo is missed. The time dependent gain monitor permits the user to monitor the minimum signal level required to trip the receiver. The receiver steadily increases the amplifier gain as it awaits the echo, since the longer the transmission time of the acoustic wave, the more attenuation that will occur.

Pulser-receiver 60 has a number of adjustment potentiometers that can be used to optimize measurement performance. The adjustment parameters that were considered important to the measurements accomplished with this setup were the maximum automatic gain control which adjusts the maximum gain the receiver can use, and the damping control which adjusts the impedance match between the receiver and transducer.

In use, the pulser-receiver variables were adjusted while observing the receiver response on the oscilloscope to maximize the fraction of echoes for which the marker was visible on the screen. Typically, whenever the automatic gain control or echo height control was adjusted, a corresponding adjustment of the damping control was required. Once a receiver setting was obtained, a complete set of data was collected for all 26 operating conditions detailed in FIG. 7 without further adjustments.

Figure 7:
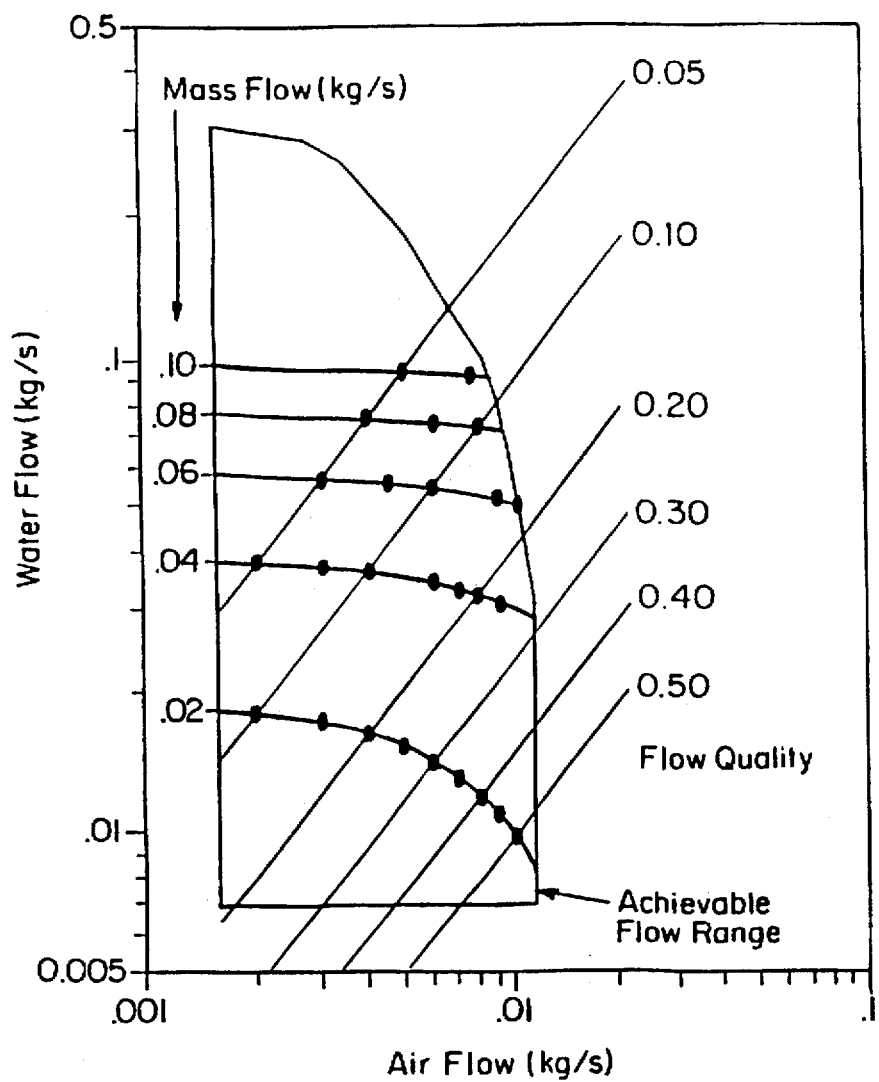
FIG. 7 is a graphical illustration of mass flow as compared to quality defining the flow conditions for a number of tests performed by the method according to this invention.

FIG. 7 is a chart of the range of qualifies and mass flows for which data was taken with this setup. The total mass flows range from 0.02 to 0.10 kg/s. The 26 test conditions are shown as dots in the figure. They were selected to cover the bulk of the achievable flow conditions with lines of constant mass flow and constant quality so that the effects of mass flow and quality could be evaluated separately. Water flow is measured using a turbine flow meter and air flow is measured using an elbow flow meter.

Figure 8:
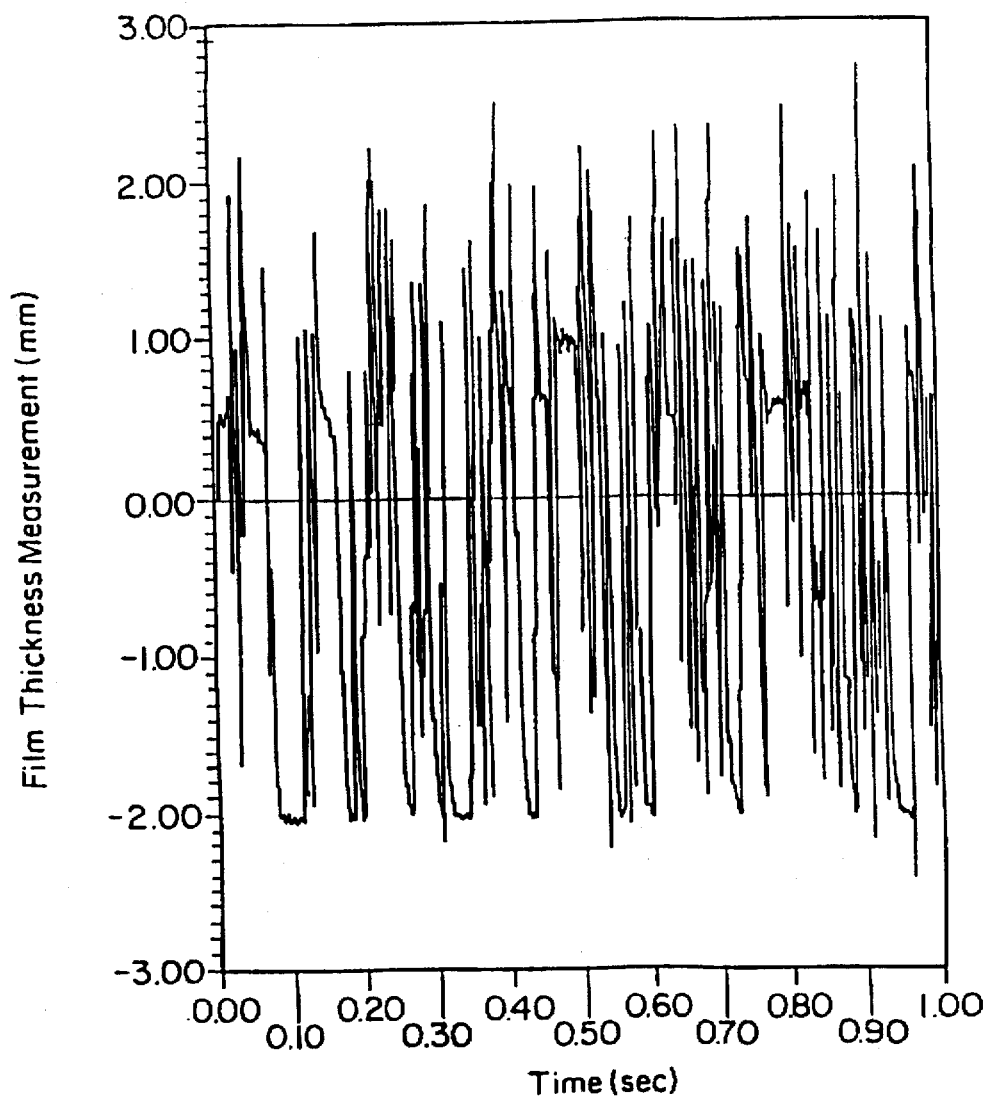
FIG. 8 is an illustrative representation of a typical ultrasonic film thickness measurement record using the measurement systems depicted in FIGS. 5 and 6.

A typical result of one portion of one record for this data collection is shown in FIG. 8. This is data for one second. Lost signals, or pulses that did not result in a recognized echo, are represented in the graph as negative readings. The data are far more rapidly varying than would be expected. Through derailed analysis, it became evident that the thickness of the film could not have varied as quickly as the data. Accordingly, it was theorized that the observed behavior probably represented a combination of steep faces of waves in the liquid film and bubbles within the liquid film that reflected and/or refracted the echoes away from the transducer so that they were lost, along with errors resulting from the lack of synchronization of the pulser-receiver and the data acquisition system.

Figure 9:
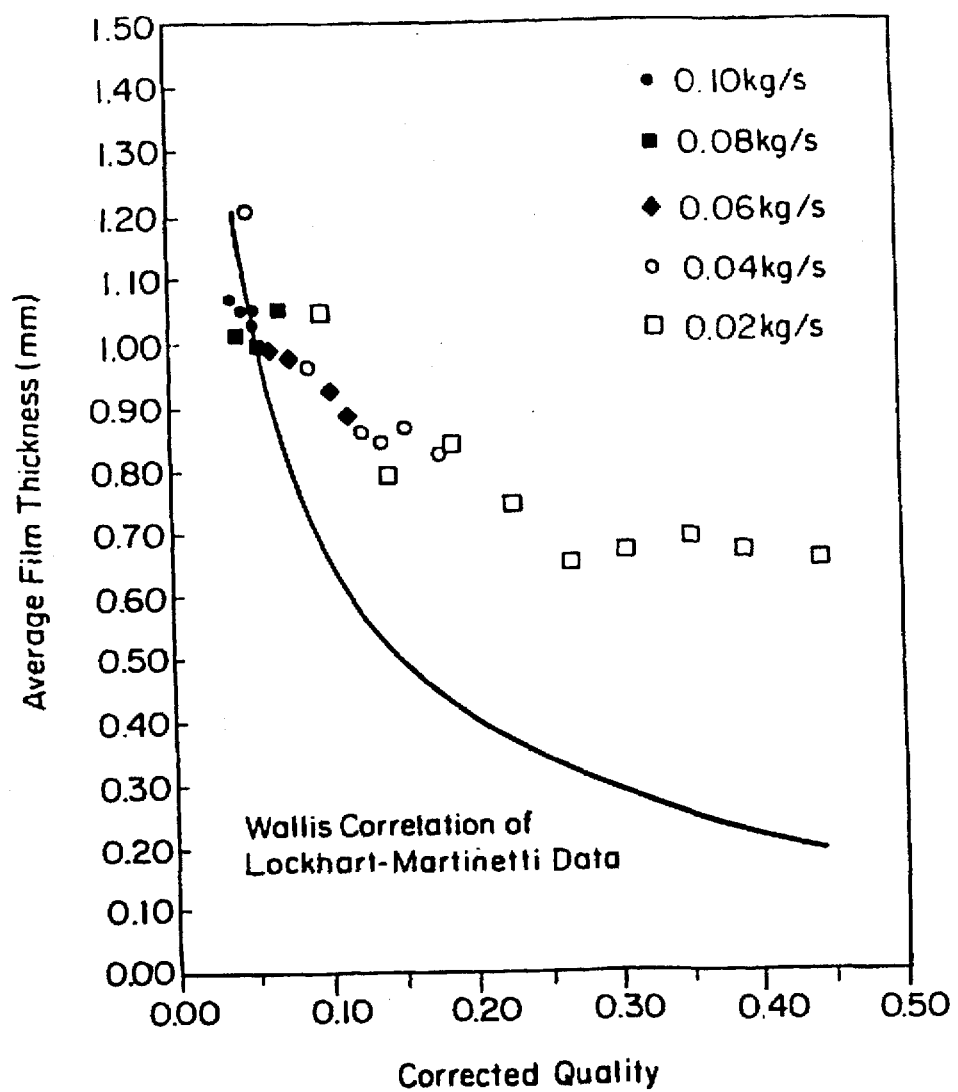
FIG. 9 is a chart of the average film thickness measurements for the test condition shown in FIG. 7 along with a published an empirical correlation based on the assumption that all the liquid is in a film with no vapor trapped in the film.

FIG. 9 is a chart of corrected quality versus average film thickness for the 26 test points of FIG. 7. The "corrected quality" was a correction applied so that the Martinelli parameter of the actual flow condition tested with actual quality was equal to that of a fictitious flow at ambient pressure with "corrected" quality. The magnitude of the correction ranged from negligible for test conditions near ambient pressure to as much as 0.059 for the highest pressure conditions. Also plotted in FIG. 9 is a Wallis correlation of the Lockhart-Martinelli data which should have been a good predictor of the correlation between corrected quality and average film thickness. As can be seen, the values obtained were generally higher than predicted, and were not of the same functional form as the predictions. Additionally, the data scatter was larger than expected, there was no clear trend of the data with mass flow, and the values for high qualities were roughly constant, implying that ultrasonic film thickness measurement may not always be a good indicator of flow quality.

Figure 10:
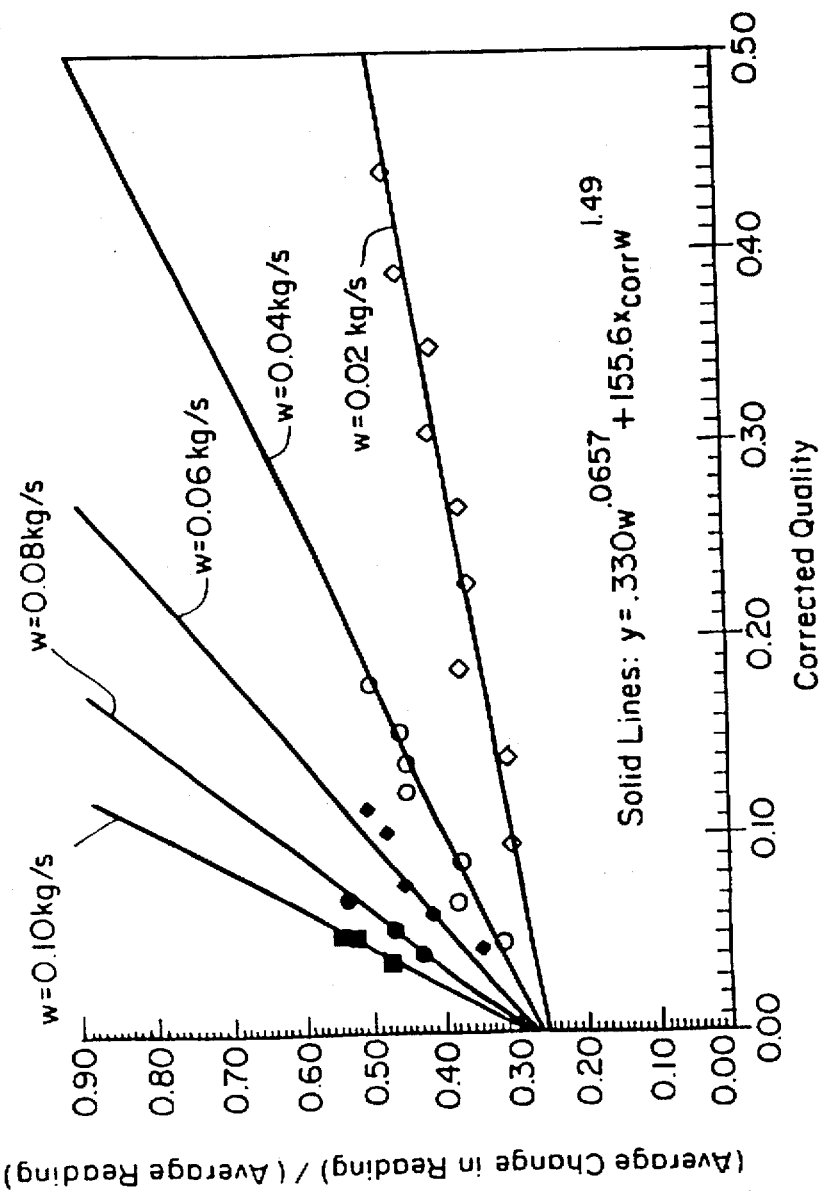
FIG. 10 is a graph of the corrected flow quality using the average change in sequential good thickness readings divided by the average thickness reading for the data plotted in FIG. 9.

FIG. 10 is a chart of the mass flow versus the fraction of recognized echoes, showing a rough trend. This indicates that the mass flow can be at least roughly determined from the number of recognized echoes compared to the number of actual pulses; the fraction of recognized echoes.

Figure 11:
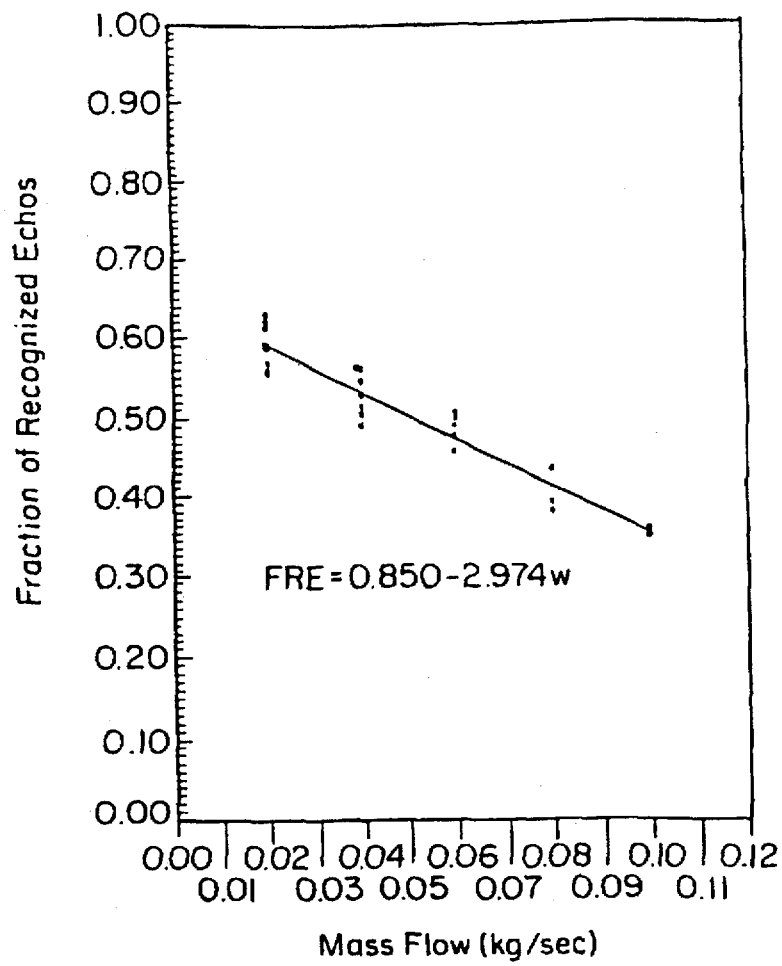
FIG. 11 is a chart of the mass flow versus the fraction of recognized echoes for the data points of FIG. 7 taken with the equipment shown in FIGS. 5 and 6.

A further analysis of the ultrasonic record data was made as follows. The "length" (L) of an ultrasonic data record may be defined as:

$$L = \sum_{i=1}^{n} |t_i - t_{i+1}|$$

where $t_i$ is the ith thickness reading and n is the number of readings. In order to account for the unrecognized echoes, this length was normalized by dividing by the number of recognized echoes. This new quantity is the average change in film thickness reading from one reading to the next. Plotted in FIG. 11 is this value normalized by the average value of the reading to place the chaotic variations into the context of scale of the value itself. This figure shows that this normalized measure of the ultrasound thickness readings is unambiguously related to the mass flow and quality of a two-phase flow.

The correlation of mass flow to the fraction of recognized echoes as established in FIG. 10 establishes that all the information required to define both mass flow and quality of a two-phase flow is present in the ultrasound records.

Referring again to FIG. 8, the following additional flow indicator quantities according to this invention are derived from the return echo thickness measurement record: the average number of good thickness readings; the average change in sequential good readings; the average fraction of readings that are good; the root mean square (RMS) of good thickness readings; the RMS change in sequential good readings; the average number of good readings in a row; the average number of bad readings in a row; and the characteristic autocorrelation time. A good thickness reading is defined such that a detected return echo is assumed to be indicative of the thickness of liquid flow in the conduit. In contrast, a bad reading is one in which a steep fluid/vapor interface deflects the return echo so that it is not detected, or where there is a fairly rough liquid/vapor interface and a return pulse above a predetermined magnitude is not detected.

In this invention, the foregoing indicator quantifies are calculated and the results fed to a neural network which applies a pattern recognition analysis to the indicator quantities and correlates the mass flow and quality of the two phase flow.

It was first realized that the indicator qauantity:

$$\frac{\text{Average Absolute Value Change in Sequential Good Readings}}{\text{Average Good Readings}} \quad (3)$$

was able to clearly discriminate mass flow from quality as can be seen in FIG. 10. If one knew the mass flow or quality, the other quantity could be determined. An early analysis revealed that the fraction of recognized echoes was found to correlate roughly with mass flow as shown in FIG. 11. Upon further investigation, however, it was realized that the ultrasonic data of FIG. 8 contained enough flow-related indicators to accurately determine mass flow and quality.

Using the mass flow indicator quantifies described above, mass flow and quality can be determined as follows. The average thickness reading is a first order indicator of flow quality and in some cases may be used alone to determine quality. The RMS thickness reading accentuates the passage of large waves within the two phase flow which are of higher importance for lower quality and higher mass flow conditions. The average fraction of recognized echoes reflects the influence of flow characteristics that result in the loss of reflected acoustic pulses. These influences result from the steepness of the liquid/vapor interface (such as with steep waves or bubbles within the liquid film) or from an irregular surface texture (such as from droplet entrainment or deposition). The average absolute value change in sequential good readings reflects small scale changes in the liquid/vapor interface. It may be indicative of either small dynamic waves (surface texture) or the rate of growth of passing large scale waves. The former case should be dominant because large waves pass relatively infrequently and a high rate of change in reading cannot be sustained over a significant observation period. Interestingly enough, changing the rate of data collection affects this value linearly, i.e. halving the data rate results in doubling the average change in sequential readings.

The RMS change in sequential good readings accentuates events with a larger scale of variation. The average number of good readings in a row reflects the average time period in which a relatively undisturbed liquid film is present. The average number of bad readings in a row reflects the average time period in which a disturbed liquid film is present. The sum of the average number of good readings in a row and the average number of bad readings in a row reflects a characteristic time period for the passage of film disturbances.

Figure 12:
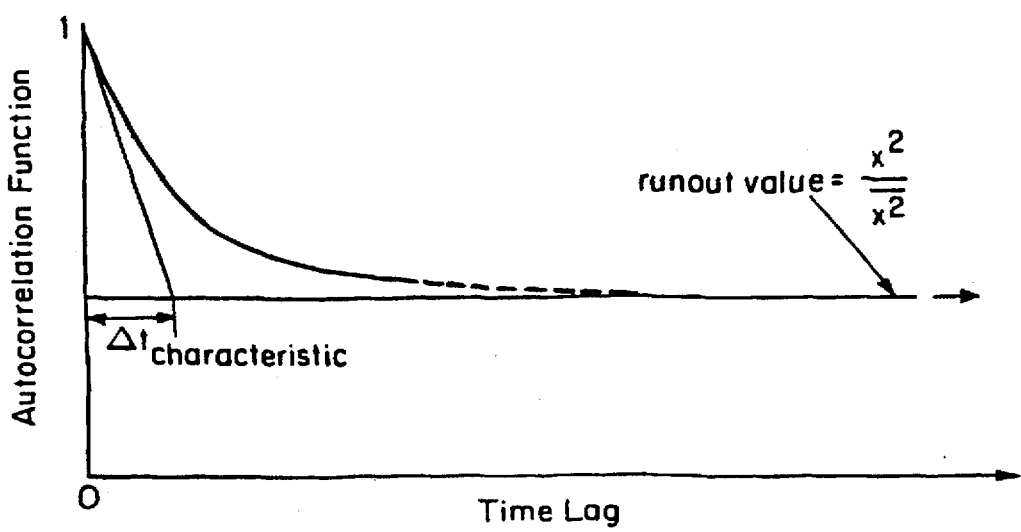
FIG. 12 is a graph of the characteristic auto-correlation time used as a flow indicator according to this invention.
Figure 14:
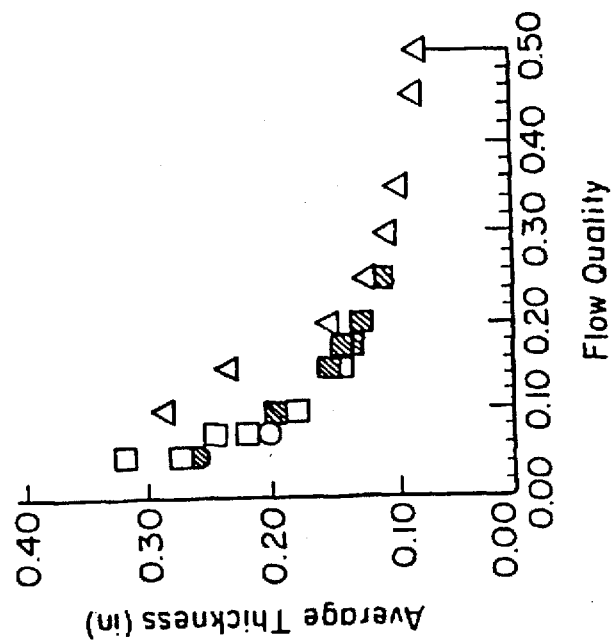
FIGS. 13–20 are graphical illustrations of the flow indicators according to this invention compared to flow quality.
Figure 13:
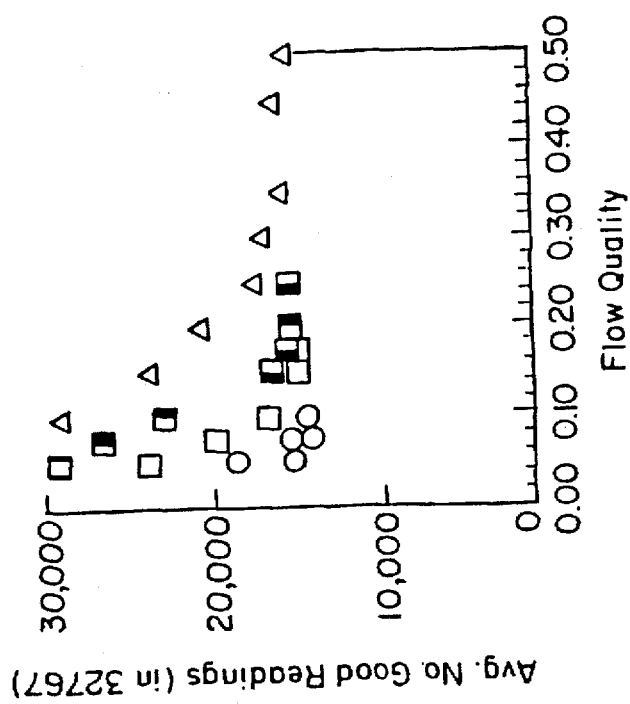
Figure 16:
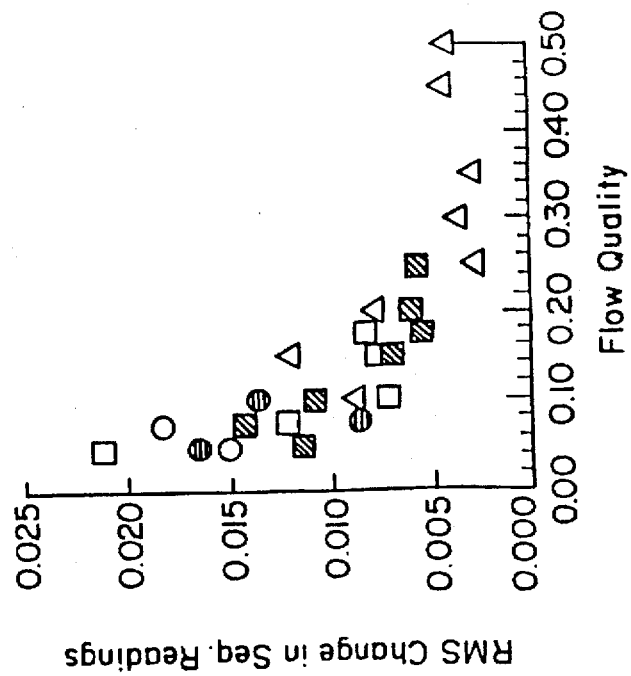
Figure 15:
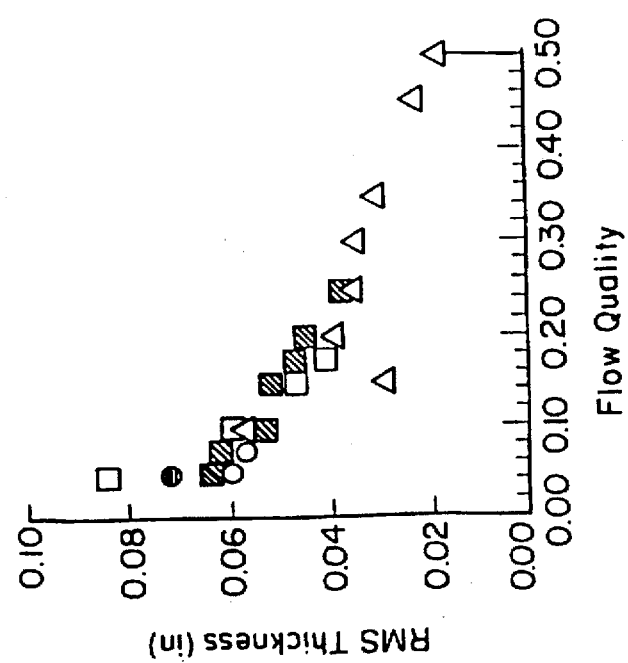
Figure 18:
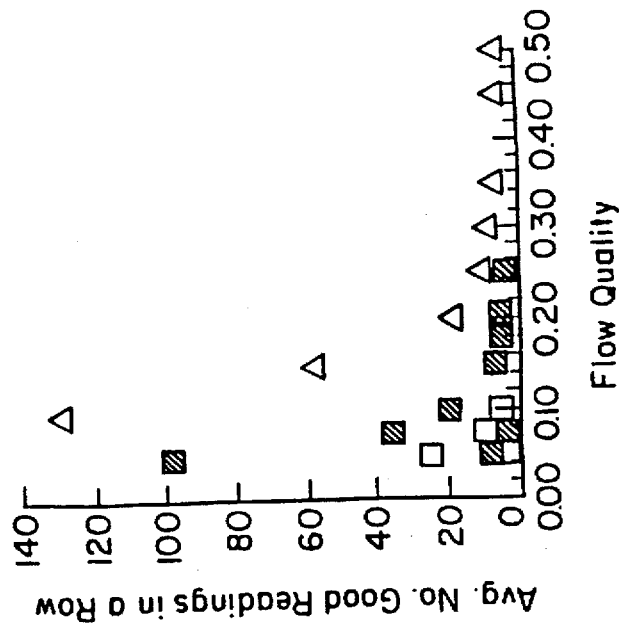
Figure 17:
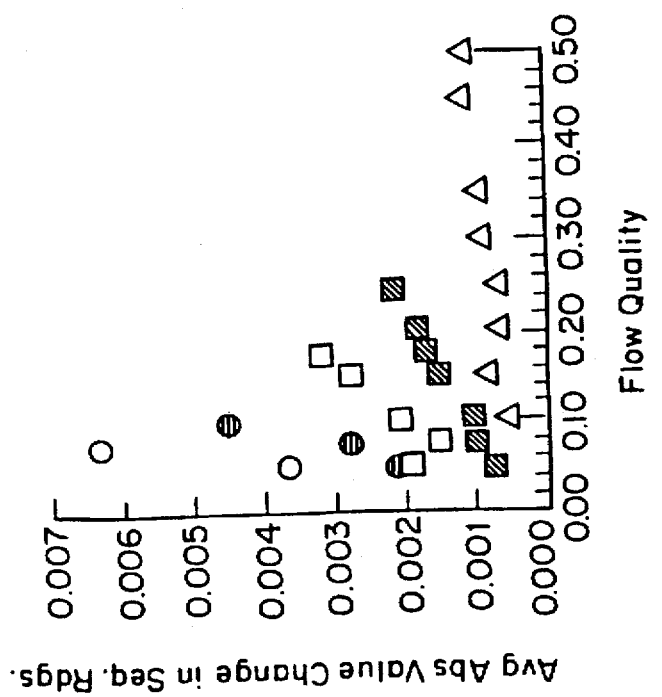
Figure 20:
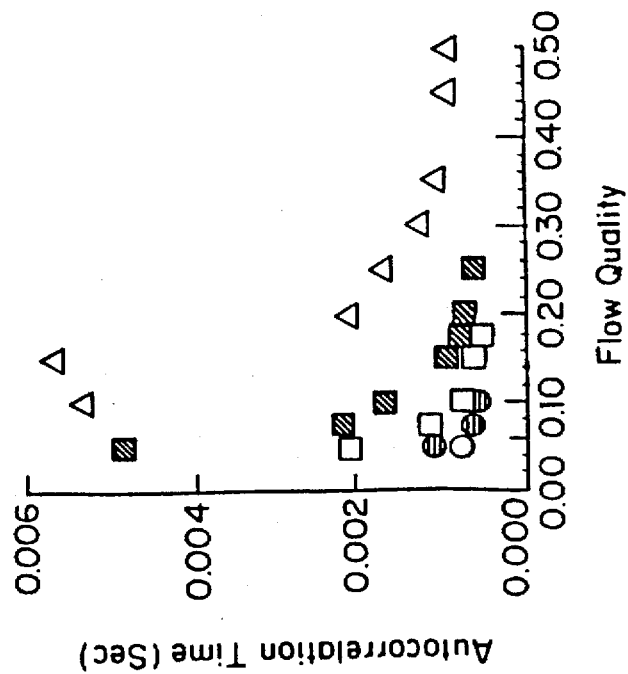
Figure 19:
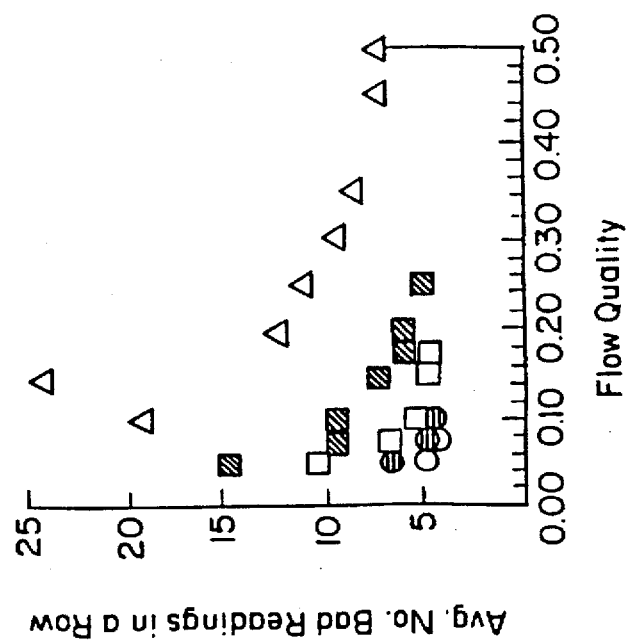

The characteristic autocorrelation time is shown in FIG. 12. In autocorrelation, a copy of a signal is time-shifted and compared with the original signal and the integral of the product of the original and time-shifted signals calculated. This process is repeated for different amounts of time-shifting (time lags). For a chaotic signal, the results typically appear as shown in FIG. 12. The characteristic autocorrelation time is an indicator of the rate at which the signal no longer "looks like itself". This indicator has been shown by others to reflect the characteristic flow velocity. (See e.g., Bernatowicz, H., Cunningham, J., and Wolff, S., "Mass Flow Meter Using the Triboelectric Effect for Measurement in Cryogenics", NASA CR-179572, April 1987).

Typical results for each of these indicator quantities are shown in FIGS. 13–20. These graphs plot each of the flow indicator quantities as a function of flow quality for horizontal flows wherein flow quality was determined by non-ultrasonic techniques i.e., the air and water flow rates were measured before they were mixed to form the two-phase flow. The different symbols correspond to the mass flows of the different test conditions. The graphs reflect twenty five combinations of mass flow and quality. When the calculations shown in FIG. 10 are performed for corresponding upflow and downflow test conditions, the results are similar but somewhat modified. Therefore, the technique according to this invention should work for different flow orientations, and also in zero gravity situations.

There are various ways in which the analysis could be implemented in a two phase flow system. The first is to take the ultrasonic data, calculate the data indicators described above (average number of good readings in a row, etc.) and, using non-linear multivariate statistical analysis to correlate the indicators to the mass flow and quality. This method may not be desirable, because it is only as accurate as the non-linear correlation methods used to model the data. In addition, such a method does not disclose whether a data set is bad, or, given bad data, does not accurately estimate the correct flow conditions. Finally, this approach will be fairly slow.

Another approach is to take the data and feed it directly to a neural network to correlate patterns within the data to the mass flow and quality. In principal, this method could provide the desired fault indication and fault-tolerance. However, such a method could be undesirable because it would be difficult to prove that the neural network was using the correct data patterns to correlate the mass flow and quality and thus the instrument would only be as good as the network training. Real world data could find niches within the network that do not correlate properly to the mass flow and quality. Also, a very large network would be required because of the many sequential readings that are needed to define the patterns. Such a large network could be slower than an explicit calculation of the indicators and statistical correlation.

Figure 21:
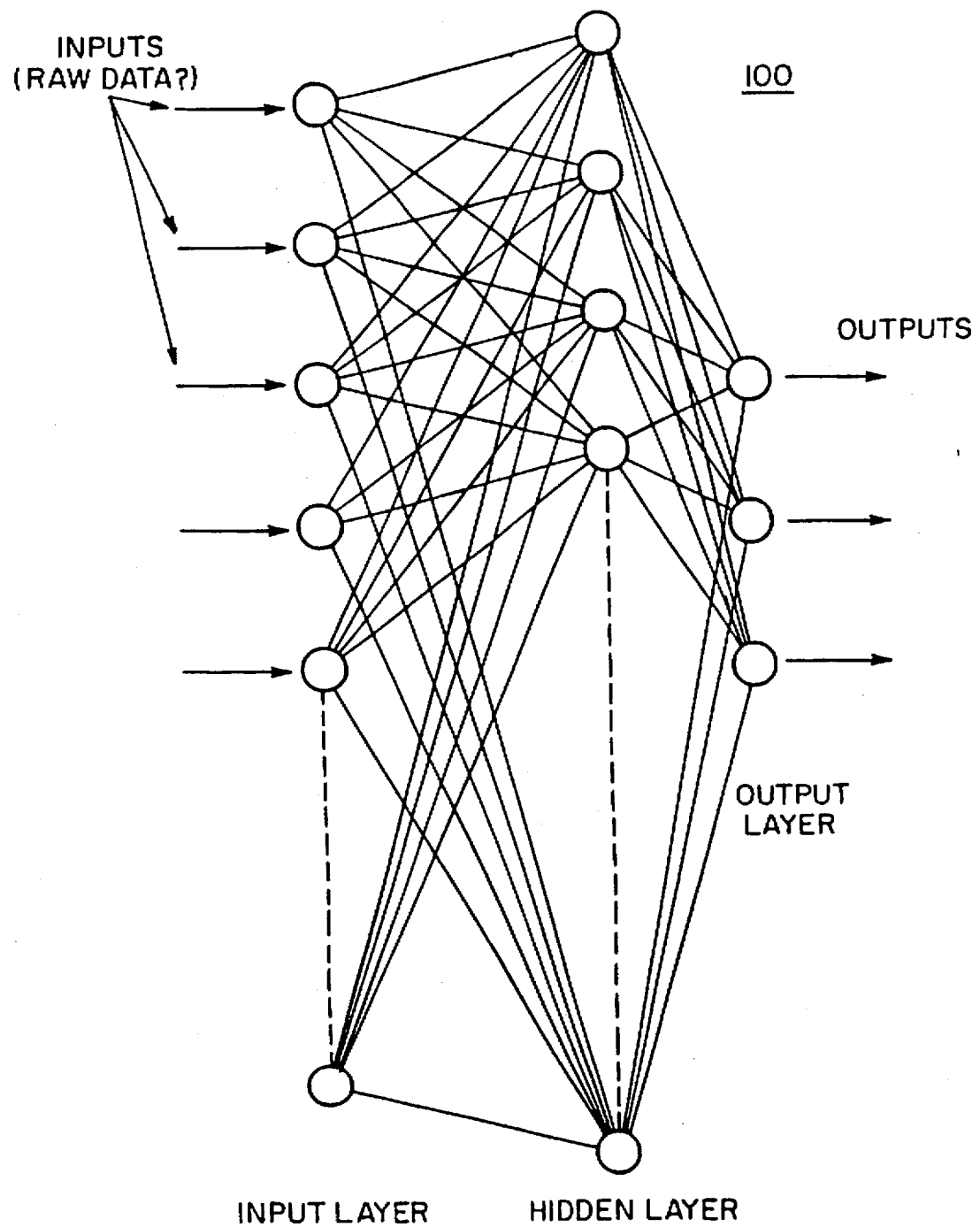
FIG. 21 is a schematic diagram of a neural network useful for pattern matching the indicators shown in FIGS. 13–20 to evaluate mass flow and/or mass quality according to this invention.

The preferred approach is to take the data, calculate the data indicators, and use neural network 100, FIG. 21 to correlate the indicators to mass flow and quality. This approach combines confidence in the data indicators with a fast, fault tolerant, nonlinear correlation achievable with a small neural network. Neural network 100 is based on a commercially available neural network simulation program "NeuroShell 2", available from Ward Systems Group of Frederick, MD.

To test this approach, the data graphs in FIGS. 13–20 where used to train neural network 100, FIG. 21 to recognize the flow conditions of the ultrasonic data. The neural network was configured as a conventional back-propagation network with eight input nodes corresponding to the eight indicator quantities of FIG. 13–20. Twelve hidden nodes were fully interconnected with these input nodes and also with two output nodes corresponding to mass flow and quality, respectively. Back-propagation training was used with various learning rates and momentum values to optimize network performance. To avoid over-training, network 100 was trained using data from only 13 of the 25 test conditions. A new network configuration was saved only if it improved the prediction of the flow conditions for the other 12 test conditions. The results of this analysis are presented in FIGS. 22 and 23. These graphs compare the actual flow conditions of the data sets with those estimated by the neural network. As the graphs show, there is an extremely good correlation between the actual and predicted values for mass flow and quality for all tests conditions. In fact, the scatter between the data points is comparable with the measurement error associated with flow conditions.

In principal, it should be possible to use a single neural network to correlate flow conditions for different conduit sizes, system pressures, and flow orientations (or zero gravity conditions). To do this, the conduit diameter, pressure, and flow orientation would be additional inputs to the neural network.

Figure 24:
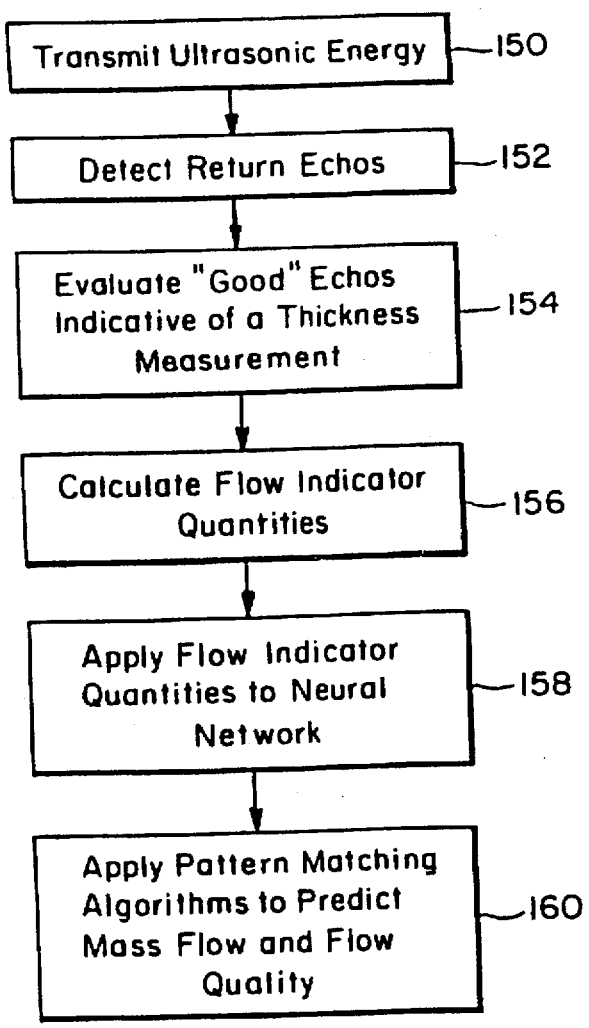
FIG. 24 is a flow chart depiction of the method of evaluating mass flow and quality according to this invention.

In summary, the method and the system for analyzing a two phase flow in a conduit is graphically depicted in the flow chart shown in FIG. 24. In step 150, ultrasonic energy is transmitted through the conduit and into the flow therein using the apparatus shown in FIG. 5 and 6, and return echoes are detected (see FIGS. 2-4), step 152.

Next, step 154, all good return echoes are evaluated. In step 156 one or more flow indicator quantifies are calculated including: the average number of good thickness readings, the average fraction of the total readings that are good, the average absolute value change in sequential good readings, the RMS of good thickness readings, the RMS change in sequential good readings, the average number of good readings in a row, the average number of bad readings in a row, and the characteristic autocorrelation time. See FIGS. 10-20. There is no intrinsic limit to the number of indicator quantities which may be used to characterize the flow. However, a large number of quantities may not improve the predictive accuracy of the instrument system, and could result in undesirably slow operation.

Figure 23:
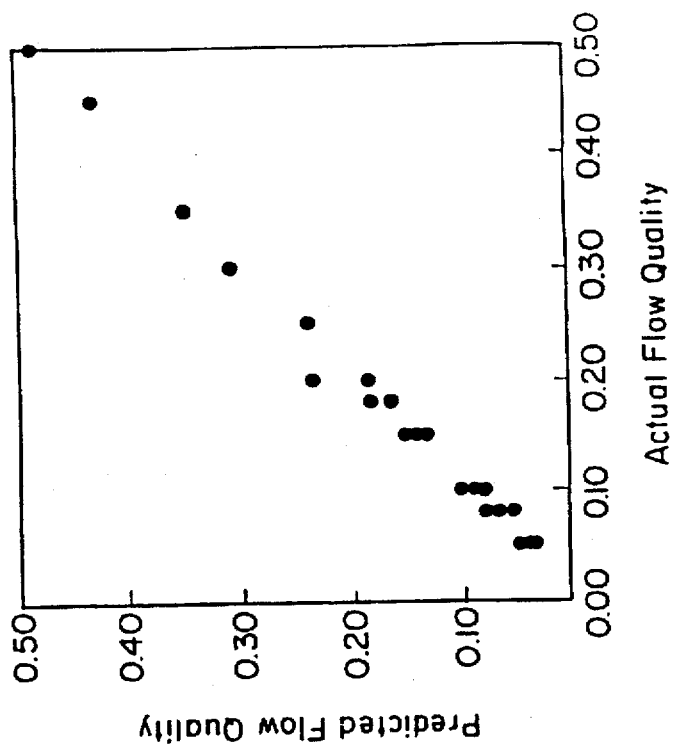
FIG. 23 is a graphical depiction of the correlation of flow quality determined according to the neural network shown in FIG. 21 compared to the predicted flow quality.
Figure 22:
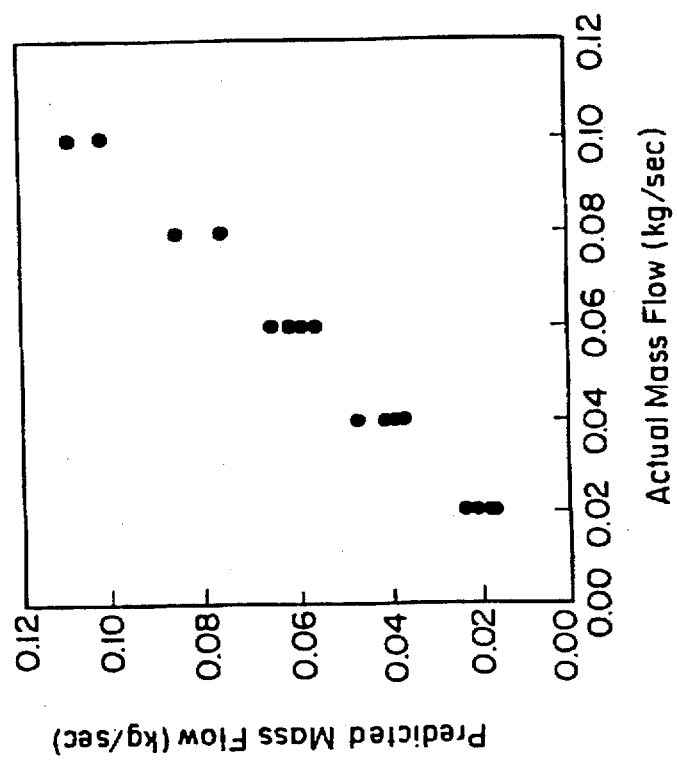
FIG. 22 is a graphical depiction of the correlation of mass flow determined according to the neural network shown in FIG. 21 as compared with the predicted mass flow.

In step 158, two or more of these flow indicator quantities are applied to neural network 100, FIG. 21, which applies pattern matching algorithms to predict mass flow and flow quality, step 160 FIG. 24 (See FIGS. 22-23).

Other Methods

Figure 26:
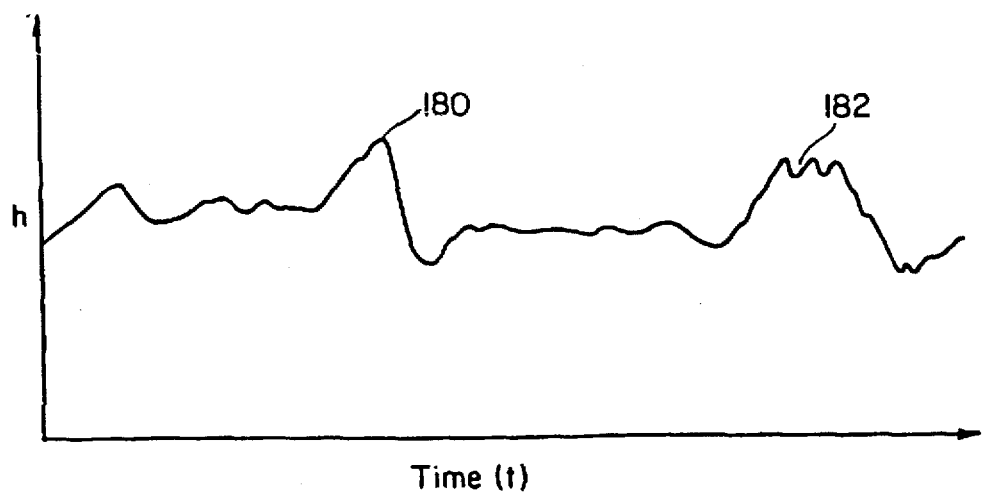
FIG. 26 is a chart of flow behavior measured by the sensing system of FIG. 25.

It was also realized that the flow indicator quantities could be derived from non-ultrasonic means. For example, capacitive sensor 170 on pipe 172 having a two phase flow 174 therein will detect changes in film thickness h over time as shown in FIG. 26. The nominal thickness will be the average of the thickness readings while the peaks as shown at 180 and 182 represent the passage of waves of liquid through the pipe.

In all embodiments, the flow indicator quantities and the definition of a "good reading" will depend on the sensor used.

Figure 25:
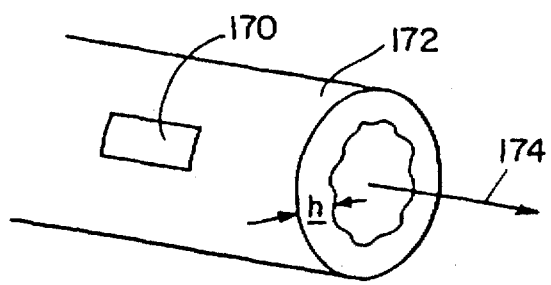
FIG. 25 is a schematic view of another type of sensing system used to evaluate a two phase flow according to this invention.

Therefore, sensing means such as capacitive sensor 170, FIG. 25 or ultrasonic transducer 16, FIG. 1 are used to make a plurality of flow observations. A number of flow indicator quantities are then calculated from the resulting data and compared with known flow conditions using, for example, the neural network shown in FIG. 21. Then, based on the comparisons, the mass flow rate and the flow quality can be determined as set forth in the discussion above in reference to FIGS. 13-17 and 22-23.

The current invention is applicable to all measurements of two-phase flows in which an observation is available that reflects the complexity of the flow behavior. While this disclosure describes a reduction to practice in which ultrasonic thickness measurements are used with liquid-gas two-phase flows, it is clear that the current invention may be used to advantage with different measurement techniques and different types of flows. The different basic types of flows include the following: liquid-vapor or liquid-gas; immiscible liquids; a liquid flow containing dispersed solids: and a vapor or gas flow containing dispersed solids.

These flows may be oriented in any direction with respect to a gravitational or other body force without limiting the applicability of the invention. The liquid-gas flows described in this disclosure were mined in horizontal flow, vertical upflow, and vertical downflow. Because of the robust discrimination of flow conditions achieved with the methods described, the current invention also would be applicable to flows inclined at arbitrary angles with respect to gravity, in the presence of reduced or enhanced gravitation, or in the absence of gravity.

Flow observation methods that currently appear capable of providing the desired reflection of flow complexity include the following: pressure or pressure drop measurements, including those using pressure transducers, microphones, and hydrophones; acceleration measurements, either of the flow duct wall or, through a protrusion into the flow, of the flow itself; length, area, or volume measurements, such as using transmission-mode or reflected-mode ultrasound, capacitance, or conductance; photon attenuation measurements, using microwaves, visible light, X-rays, or gamma rays; species passage measurements, such as through triboelectric observations, neutron irradiation, or nuclear magnetic resonance; velocity measurements, such as through acoustic or optical velocimetry; and acoustic density measurements.

Other measurement methods will occur to those skilled in the arts of two-phase flows and instrumentation. These measurements may be implemented in an extremely broad range of geometries and embodiments. For example, a pressure drop measurement may be made between two points on a straight section of a flow duct, between the taps of a venturi, orifice, or pitot-static tube, between the inside and outside radius of an elbow, etc. The number of possible such arrangements is unlimited. The current invention enables flow measurement whenever the variation in the flow observation is used to determine a flow-related quantity.

Data that meaningfully reflect turbulent flows are highly complex and uneven in nature. For example, most two-phase flows include fluctuations that may be viewed as waves of one form or another. The size, shape, and speed of a given wave depends upon the local conditions of the flow, which vary chaotically. Thus the waves are not periodic, but are better described as occasional. By the same token if one were to observe the passage of many such waves, one would find a well-defined distribution of wave characteristics for a given flow condition. As the flow condition varies, this distribution varies accordingly. Thus, if the distribution of flow fluctuations is properly characterized, it can be used to define the flow condition. This is the primary objective of the current invention.

A key factor in successfully discriminating flow conditions from time series data is identifying features in the data that reflect important flow phenomena. In some cases, key phenomena are reflected in the average of a measurement signal. For example, the average thickness of the liquid film in liquid-gas two-phase flows is a valuable indicator. In other cases, the average value of a signal does not convey significant information. This would be the case in an acceleration measurement, where the average value normally is zero. In any event, more than one data feature must be extracted to define the flow. The reasons for this are the following: Since a two-phase flow is actually two concurrent flows, more than one quantity is needed to define the flow condition (e.g., flows of phase A and phase B).

Each data feature results from the total condition of the flow, and cannot be attributed to a single flow phenomenon of interest (e.g. average film thickness in liquid-gas gas two-phase flows is related to both the liquid and gas flow rates).

A certain amount of redundant information improves the correlation of the flow conditions. This is because only a limited amount of data can be used to calculate a given flow indicator in most practical applications: one normally has access to data for a fraction of a second or a few seconds of readings, rather than huge quantities of data collected over an extended period of time. Thus, if two or more data features reflect similar information about a flow phenomenon, using more data indicators generally will improve correlation accuracy.

Aside from an average value of a measurement, the data features of interest are derived from the temporal variation of the data. The simplest characterization of the variation of the data is the standard deviation. In addition, waves have many features of their size, shape, and evolution that can be exploited to discriminate one flow condition from another. The two easiest observations to make about a wave in time series data are its size and period or time of passage. There are many ways to characterize these features in a given time series. Some of these are described below. There are many more such measures present in the data that will occur to those skilled in the arts of two-phase flows, statistics, or instrumentation.

Simple measures of the size and duration of a wave are the signal amplitude, the cumulative positive or negative departure from signal means, and passage time. While it may seem a simple matter to define these quantities from a time series signal, this is often difficult to do, particularly with highly irregular chaotic data. For example, it often is difficult to pick out the peak of a wave from smaller scale local peaks. For that matter, it often is difficult to define what constitutes one large wave or several smaller waves. This raises a critical issue that is intrinsic to chaotic systems: important phenomena generally occur over a broad range of physical and time scales. In principle, the phenomena occur over all scales: one form of fractal analysis characterizes the distribution of phenomena with scale to characterize the underlying system behavior. In many cases, characterizing a phenomenon at one scale provides a meaningful flow indicator. In other cases, particularly to permit discriminating a very broad range of flow conditions, the variation of the phenomenon with scale may be needed. For these cases, characterizing phenomena over a small number of scales (e.g., two) provides the bulk of the information contained in the continuum of scales. Thus a limited degree of multi-resolution analysis may enhance discriminating flows from time series data. This is most easily achieved by sorting or filtering the data to examine features occurring at the different scales of interest.

A method to discriminate the largest scale of amplitude is described as follows.

First, the mean and standard deviation of the data set are calculated. All points at which the data history crosses the lines (mean+standard deviation) and (mean-standard deviation) are noted. The use of standard deviation as the "gating" value is somewhat arbitrary: while it has the advantage of reflecting the overall variability of the data set, there is no intrinsic reason to select it rather than another value. The highest value encountered between crossings of (mean+standard deviation) and the lowest value encountered between crossings of (mean-standard deviation) are noted for all such occurrences, and averaged. The results may be called "average peak" and "average trough".

The difference between average peak and average trough may be used as a measure of amplitude of the largest wave scale.

The average amplitude described above may not always provide the most sensitive discrimination of large scale events. In cases where the largest scale events are most important, the indicator quantity should reflect the largest amplitude more than the average amplitude. In this case, an rms (root-mean-squared) amplitude may be used. This may be calculated either using the rms of peak values and rms of trough values and finding the difference, or calculating the rms of (peak-trough) values. In cases where successive peaks and troughs are uncorrelated, the second method should produce slightly larger, but similar results to the first method. In the rare case where the values of peaks and troughs vary in such a way that amplitude is relatively steady, the second method will better reflect the nature of the system variation.

The previous statement may be generalized to permit events of different scales to be relatively enhanced or suppressed. In this method, the various observations are weighted as follows:

$$\overline{x}_k = \left[ \frac{1}{n} \sum_{i=1}^{n} (x_i)^k \right]^{\frac{1}{k}} \quad (4)$$

For k=1, a simple mean is calculated, which weighs each value evenly. For k=2, the rms is calculated, which weights large values more strongly. For values of k less than 1, small values are accentuated.

In many cases, the high frequency "noise" may be of sufficient amplitude that virtually any pair of successive readings represents a crossing of a standard deviation line. This high frequency may represent either a high degree of small scale system behavior or random instrument noise. When this is found, it is necessary to smooth the data. One way to accomplish this is by taking a moving average of the data, i.e., $$\overline{X}_i = \frac{1}{n} \sum_{j=1}^{n} X_{i+j-1} \quad (5)$$

where n is the averaging window. The averaging window size is chosen so that it spans more than one full period of the high frequency "noise", often only several sampling intervals (e.g., n=10). This process is simple and quick to implement, and results in a much smoother data set that promotes calculation of the large scale data indicators.

In some cases, the amplitude of a given wave is meaningless without the context of the overall signal history. For example, the signal obtained using the triboelectric effect depends on the naturally occurring electric charges present in the fluid. The level of charge depends on uncontrollable factors often not intimately related to the flow condition. Thus, it would not be appropriate to use the value of the amplitude without normalizing it to some measure of average signal variation. One obvious such measure is the standard deviation of the signal.

The foregoing method provides just one way to characterize large scale signal amplitude. One potential enhancement is to consider only those crossings of one standard deviation line that are preceded or followed by a crossing of the other line. In this way, only the large events that cover the bulk of the system variation are considered. Other methods of characterizing amplitude will occur to those skilled in the relevant arts.

Another way of characterizing a large wave is by the area it encloses (integral with respect to time). This combines the effects of the amplitude and duration of the wave. In this method, the signal is integrated (or summed) between crossings of the average amplitude point (both positive and negative), and each value recorded. The averages of both the positive and negative integrals are calculated. The difference between the average positive and negative integrals characterizes the average wave size. Enhancements to this method include the following: First, calculate integrals only for those events that exceed the standard deviation lines. Second, calculate integrals only of the part that exceeds the standard deviation lines. Third, calculate rms of integrals to accentuate large scale events. Clearly, many other analogous quantities will occur to those skilled in the relevant arts.

Another key characteristic of a wave is its period of duration in time. If the preceding quantities have been calculated, then the first such measure can be calculated by dividing the area-measure by the amplitude-measure. Another basic method is the following. First, sort the data set to note the points at which the standard deviation line. are exceeded. Second, calculate the time differences between crossings of each line. Third, average the time differences for both the positive and negative standard deviation crossings. The sum of these is a measure of the duration of large waves.

There are many possible enhancements to this measure. These include the following: First, calculate the time difference between "rising" crossing of the positive standard deviation line and the next rising crossing (and similarly for the negative deviation lines). The average or weighted average of these time differences better characterizes longer wave periods. Second, calculate the time differences between a "rising" crossing of the positive standard deviation line that follows a crossing of the negative deviation line and the next similar crossing. An average or weighted average of this figure (possible combined with the negative version of this fixture) more forcefully accentuates large time-scale events.

Another measure of the large scale waves, which is inevitably derived during the calculation of the other measures, is the number of large scale events. Taken together, the measures of size, duration, and number of large scale events provide a meaningful characterization of the large scale flow behaviors.

Analogous characterizations of small scale waves are also useful to discriminate flow conditions. As was mentioned before, the data may include a high frequency "noise". This may reflect instrument noise or electromagnetic interference, or may be a real system behavior. It is often difficult to determine which of these is the case. One meaningful test is to record data without flow in the duct to see whether the high frequency behavior is present. If so, then it is not related to the flow and must be filtered or smoothed out. If not, then it may reflect a real flow behavior that can be exploited in discriminating flow conditions.

If filtering or smoothing is needed, the moving average technique described earlier can be used. The objective is to remove the noise component without destroying underlying flow information. Some numerical experimentation may be needed to achieve a reliable smoothing scheme. For example, moving averages of various window sizes can be calculated for a no-flow data set in which all non-zero readings represent noise. A window size can be selected to minimize the departure from zero. Any variation remaining in a smoothed no-flow data set can be viewed as a lower bound for the scale of phenomena that can be meaningfully observed with the instrument.

Once a suitable data set is obtained (possibly smoothed), small scale behaviors can be examined. The smallest scale of fluid flow behavior generally occurs well below the resolution of practical measurement instruments. At the scale of instrument resolution, small scale events may be manifested as a pervasive "texture" that varies with flow condition. The simplest measure of this texture is the average change in sequential readings, $$\overline{\Delta X} = \frac{1}{N} \sum_{i=1}^{N} |X_i - X_{i-1}| \qquad (6)$$

Here, the absolute value is used to characterize the change from reading to reading. As before, this average could be weighted to emphasize larger or smaller scale events. If data smoothing has been used, there is no point to calculating this quantity for step sizes smaller than the averaging window size, as this would reintroduce the noise that the moving average sought to reject.

Another quantity that can be used to characterize a chaotic data set is the characteristic autocorrelation time. This quantity draws on lessons learned in time-domain analysis. The autocorrelation function is calculated by time-shifting one copy of a data set by a "time lag" and summing the product of corresponding values:

$$C_{xx}(j) = \frac{1}{n-j} \sum_{i=1}^{n-j} [X_i (X_{i+j})] \qquad (7)$$

This function is often normalized so that the value for a zero time lag (j=0) is unity. A typical (unnormalized) autocorrelation function for chaotic data is illustrated in FIG. 12. The value for zero time lag is $$C_{xx}(0) = \frac{1}{n} \sum_n X_i^2 = \overline{X^2} \qquad (8)$$

(See e.g., Bernatowicz, H., Cunningham, J., and Wolff, S., k"Mass Flow Meter Using the Triboelectric Effect for Measurement in Cryogenics", NASA CR-179572, April 1987). The uncorrelated "runout" behavior is $$C_{xx}(\infty) = \left[ \frac{1}{n} \sum_n X_i \right]^2 = \overline{X}^2 \qquad (9)$$

The characteristic autocorrelation time is the initial rate at which the autocorrelation of the data set leaves the initial point and approaches the "runout" behavior. The characteristic autocorrelation time has been related to the velocity of a flow [8]. For many time series data, $\Delta t_{characteristic} \gg \Delta t$ sample, so it can be easily approximated by $$\Delta t_{characteristic} = n \Delta t_{sample} \frac{\overline{X^2} - C_{xx}(n \Delta t_{sample})}{\overline{X^2} - \overline{X}^2} \qquad (10)$$

where $\Delta t_{sample}$ is the data sampling interval and n the number of samples by which one copy of the signal is "slipped" to calculate the initial slope. In many cases, it is sufficient to use n=1 resulting in a simple, easily implemented calculation algorithm. While the result obtained varies with n and sampling time, the results obtained with a given set of calculating parameters vary smoothly with flow conditions. Thus, it is more important to consistently apply a single calculation algorithm than to use the most accurate algorithm.

An important factor only briefly mentioned to this point is the sampling rate or sampling interval. The main consideration for successfully relating the flow observations to the flow conditions is a "sufficient" sampling rate. In this context, sufficiency means that the features available in the data provide a meaningful reflection of the flow state. One means of determining the required sampling rate is through numerical experimentation. If data are collected at the highest available rate (subject to limitations of the observation method, data acquisitions equipment available, etc.), they can be examined to determine the effect of sampling rate on flow sensitivity. This can be done by calculating the various indicator quantities using each measurement, every second measurement, every third measurements, and so forth. By plotting the values of each indicator quantity against measurement interval for various flow conditions, a good compromise sampling rate can be found. Such a compromise takes into account the relative costs of computing and data acquisition hardware and required analysis rate against the benefits of improved response rate and measurement sensitivity. Considerations such as the following can be expected in this examination.

A given indicator quantity should remain steady or vary smoothly with sampling interval. As the sampling interval grows large, this smoothness may break down. This may occur either because the sampling interval is simply too large, reducing sensitivity, or because only a small number of observations are used in calculating the indicator quantity (e.g., if the sampling interval is 10, only one-tenth as many points are available as for an interval of 1). Either of these reasons may be sufficient to choose a sampling rate: while intrinsic sensitivity is a clear-cut reason to choose sampling rate, data sufficiency is similarly important. If a given instrument update rate is desired or required, then the sampling rate must be sufficient to permit valid indicator quantifies to be calculated.

The plots of indicator quantity with sampling interval should differ for different flow conditions. As sampling interval increases, the different flow conditions should be reflected by different values of the indicator quantities. For large sampling intervals, this can break down, resulting in the indicator quantity curves bunching or crossing one another. A desirable sampling rate is high enough to avoid this problem.

The final determinant of the sufficiency of a sampling rate is in the ability to relate the data indicators to flow conditions. Thus, it may be worthwhile to correlate data to flow conditions several times using indicator quantities calculated with different sampling intervals. The quality of the resulting correlations provides a firm indication of the sufficiency of different sampling rates.

Once a set of indicator quantities has been calculated for data collected for each of a representative set of known flow conditions, these indicator quantities can be correlated to the flow conditions.

Therefore, although specific features of the invention are shown in some drawings and not others, this is for convenience only as some feature may be combined with any or all of the other features in accordance with the invention.

And, other embodiments will occur to those-skilled in the art and are within the following claims:

What is claimed is:

1. A method of determining the quality of a two-phase flow in a conduit, comprising:
   transmitting acoustic energy through the conduit wall and into the flow therein to generate from the flow return echoes;
   detecting the return echoes from the flow; computing the two-phase flow mass flow rate; and
   determining from the return echoes at least one of the mass flow rate and the flow quality.

2. The flow quality determination method of claim 1 in which transmitting acoustic energy includes providing ultrasonic pulses to the outer conduit wall.

3. The flow quality determination method of claim 1 in which detecting return echoes includes determining the fraction of echoes above a predetermined echo strength.

4. The flow quality determination method of claim 3 in which determining the mass flow rate includes resolving the two-phase flow rate from the fraction of return echoes above the predetermined echo strength.

5. The flow quality determination method of claim 1 in which determining the flow quality includes calculating the liquid film thickness on the conduit from the return echoes.

6. The flow quality determination method of claim 5 in which determining the flow quality further includes calculating the average change in calculated liquid film thickness.

7. The flow quality determination method of claim 6 in which determining the flow quality further includes determining the average calculated film thickness.

8. The flow quality determination method of claim 7 in which determining the flow quality further includes determining the ratio of the average change to the average film thickness.

9. The flow quality determination method of claim 1 in which determining flow quality includes calculating one or more flow indicator quantities from the detected return echoes from the flow.

10. The flow quality determination method of claim 9 in which said flow indicator quantities include one or more of: the average number of good thickness readings, the average change in sequential good readings, and the average fraction of the total readings that are good readings, wherein a good reading is defined as a detected return echo, assumed indicative of the thickness of liquid flow in the conduit.

11. The flow quality determination method of claim 10 further including calculating the quantity of the average absolute value change in sequential good readings divided by the average number of good readings for discriminating between mass flow and quality.

12. The flow quality determination method of claim 10 in which said flow indicator quantities further include the RMS of good thickness readings, the RMS change in sequential good readings, the average number of good readings in a row, the average number of bad readings in a row, and the characteristic autocorrelation time.

13. The flow quality determination method of claim 1 in which determining the mass flow rate and the flow quality further includes applying one or more of said flow indicator quantities to a neural network for matching said flow indicator quantities with known flow conditions.

14. A system for determining the quality of a two-phase flow in a conduit, comprising:
   means for transmitting acoustic energy through the conduit wall and into the flow therein to generate from the flow return echoes;
   means for detecting the return echoes from the flow; and
   means for computing the two-phase flow mass flow rate; and
   means for determining from the return echoes at least one of the mass flow rate and the flow quality.

15. The system of claim 14 in which said means for transmitting acoustic energy includes providing ultrasonic pulses to the outer conduit wall.

16. The system claim 14 in which said means for detecting return echoes includes determining the fraction of echoes above a predetermined echo strength.

17. The system of claim 16 in which said means for computing the mass flow rate includes means for resolving the two-phase flow rate from the fraction of return echoes above the predetermined echo strength.

18. The system of claim 14 in which said means for determining includes means for calculating the liquid film thickness on the conduit from the return echoes.

19. The system of claim 18 in which said means for determining further includes means for calculating the average change in calculated liquid film thickness.

20. The system claim 19 in which said means for determining further includes means for calculating the average calculated film thickness.

21. The system of claim 20 in which said means for determining further includes means for calculating the ratio of the average change to the average film thickness.

22. The system claim 14 in which said means for determining includes means for calculating one or more flow indicator quantities from the return echoes.

23. The system of claim 22 in which said flow indicator quantities include one or more of the average number of good thickness readings, the average change in sequential good readings, and the average fraction of the total readings that are good readings, wherein a good reading is defined as a detected return echo, assumed indicative of the thickness of liquid flow in the conduit.

24. The system of claim 22 further including calculating the quantity of the average absolute value change in sequential good readings divided by the average number of good readings for discriminating between mass flow and quality.

25. The system of method of claim 23 in which said flow indicator quantities further include the RMS of good thickness readings, the RMS change in sequential good readings, the average number of good readings in a row, the average number of bad readings in a row, and the characteristic autocorrelation time.

26. The system of claim 14 in which said means for determining the flow quality further includes a neural network for matching said flow indicator quantities with known flow conditions.

27. A method for determining the mass flow rate and quality of a two-phase flow in a conduit, comprising:

transmitting acoustic energy through the conduit wall and into the flow therein to generate from the flow return echoes;

detecting the quantity of return echoes above a predetermined echo strength;

determining from the quantity of return echoes the two-phase flow mass flow rate;

calculating from the return echoes the liquid film thickness on the conduit wall; and determining the average change in calculated liquid film thickness, the average calculated film thickness, and the flow quality from the ratio of the average change to the average film thickness.

* * * * *